United States Patent
Cowley et al.

(10) Patent No.: US 10,336,731 B2
(45) Date of Patent: Jul. 2, 2019

(54) SUBSTITUTED 1H-INDOLE-2-CARBOXAMIDE COMPOUNDS AS INDOLEAMINE-2,3-DIOXYGENASE INHIBITORS

(71) Applicants: Merck Sharp & Dohme Corp., Rahway, NJ (US); IOmet Pharma Ltd., Edinburgh, Midlothian, Scotland (GB)

(72) Inventors: Phillip M. Cowley, Edinburgh (GB); Yongxin Han, Needham, MA (US)

(73) Assignees: Merck Sharp & Dohme Corp., Rahway, NJ (US); Iomet Pharma Ltd. (GB)

( * ) Notice: Subject to any disclaimer, the term of this patent is extended or adjusted under 35 U.S.C. 154(b) by 0 days.

(21) Appl. No.: 15/760,697

(22) PCT Filed: Sep. 12, 2016

(86) PCT No.: PCT/US2016/051221
§ 371 (c)(1),
(2) Date: Mar. 16, 2018

(87) PCT Pub. No.: WO2017/048612
PCT Pub. Date: Mar. 23, 2017

(65) Prior Publication Data
US 2018/0258075 A1    Sep. 13, 2018

(30) Foreign Application Priority Data
Sep. 16, 2015   (GB) .................................. 1516411.4

(51) Int. Cl.
*C07D 403/12*   (2006.01)
*A61K 31/404*   (2006.01)
*C07D 209/30*   (2006.01)
*A61K 31/4155*  (2006.01)

(52) U.S. Cl.
CPC .......... *C07D 403/12* (2013.01); *A61K 31/404* (2013.01); *A61K 31/4155* (2013.01); *C07D 209/30* (2013.01)

(58) Field of Classification Search
CPC .............. A61K 31/404; A61K 31/4155; C07D 209/30; C07D 403/12
See application file for complete search history.

(56) References Cited

U.S. PATENT DOCUMENTS

2011/0136807 A1   6/2011   Hangauer, Jr.

FOREIGN PATENT DOCUMENTS

| WO | 2015082499 | 6/2015 |
| WO | 2015150097 | 10/2015 |
| WO | WO 2015/150097 | * 10/2015 |

OTHER PUBLICATIONS

Cancer definition in MedicineNet.com—2005—p. 1.*
Stomach cancer—Mayoclinic.com—Apr. 9, 2011.*
GastricMALTLynnphonna—LymphomaAssociation—2011.*
"Adult Brain Tumors Treatment", National Cancer Institute, pp. 1-21 (Jan. 24, 2013).*
Types of Brain Cancer at http://www.cancercenter.com/brain-cancer/types-of-brain-cancer.cfm (Mar. 12, 2013).*
"Colorectal Cancer" at cancer.net (published Sep. 2012), pp. 1-2.*
"Types of Breast Cancer", published in breastcancer.org (Sep. 30, 2012); p. 1.*
Cancer Drug Design and Discovery; Neidle, Stephen, ed. (Elsevier/Academic Press, 2008) p. 428.*
Johnson et al. (British J. of Cancer, 2001, 84(10):1424-1431).*
Lens (Br. J. Nurs., 2008, vol. 17, No. 5, pp. 300-305).*
Divers et al. (Cutis. 2004, vol. 73, No. 4, pp. 257-262.*
Dolusic, Discovery and preliminary SARs of keto-indoles as novel indoleamine 2,3-dioxygenase (IDO) inhibitors, European Journal of Medicinal Chamistry, 2011, 3058-3065, 46.
International Search report appl PCTUS16/51221 dated Dec. 7, 2016, 8 pages.
Onajole, Preliminary Structure_Activity Relationships and Biological Evaluation of Novel Antitubercular Indolecarboxamine Derivatives Against Drug-Susceptible and Drug-Resistant M. tuberculosis Strains, J. Med. Chem, 2013, 4093-4103, p. 4097, Table 1, 56-10.

* cited by examiner

*Primary Examiner* — Valerie Rodriguez-Garcia
(74) *Attorney, Agent, or Firm* — Yong Zhao; Catherine D. Fitch

(57) ABSTRACT

Provided is a compound having formula (I): wherein $R^2$ is selected from $-C^1$, $-Br$ and $-CN$; $R^1$ and $R^4$ are independently selected from H and $-F$; $R^{631}$, $R^{632}$, $R^{641}$ and $R^{642}$ are independently selected from $-H$, $-F$ and substituted or unsubstituted $C_1$-$C_3$ alkyl groups; and $R^{651}$ and $R^{652}$ are independently selected from H and substituted or unsubstituted $C_1$-$C_3$ alkyl groups and substituted or unsubstituted phenyl groups; and wherein at least one of $R^{631}$, $R^{632}$, $R^{641}$, $R^{642}$ and $R^{652}$ is not $-H$, or wherein when all of $R^{631}$, $R^{632}$, $R^{641}$, $R^{642}$ and $R^{652}$ are $-H$, $R^{651}$ is not Me or Et.

11 Claims, 2 Drawing Sheets

SUBSTITUTED 1H-INDOLE-2-CARBOXAMIDE COMPOUNDS AS INDOLEAMINE-2,3-DIOXYGENASE INHIBITORS

CROSS-REFERENCE TO RELATED APPLICATIONS

This application is a U.S. National Phase application under 35 U.S.C. § 371 of PCT Application No. PCT/US2016/051221, filed Sep. 12, 2016, which published as WO 2017/048612 A1 on Mar. 23, 2017, and claims priority from GB Patent Application Numbers 1516411.4, filed Sep. 16, 2015.

BACKGROUND OF THE INVENTION

The present invention relates to indoleamine-2,3-dioxygenase (IDO) inhibitors, and in particular IDO inhibitors for use in medicine. The inhibitors of the invention may be used in pharmaceutical compositions, and in particular pharmaceutical compositions for treating a cancer, an inflammatory condition, an infectious disease, a central nervous system disease or disorder and other diseases, conditions and disorders. The invention also relates to methods of manufacture of such inhibitors, and methods of treatment using such inhibitors.

Tryptophan Metabolism—

The kynurenine pathway (KP) is responsible for >95% of the degradation of the essential amino acid tryptophan. The kynurenine pathway for tryptophan metabolism leads to the production of the essential pyridine nucleotide NAD+ and a number of neuroactive metabolites, including kynurenine (KYN), kynurenic acid (KYNA), the neurotoxic free-radical generator 3-hydroxykynurenine (3-HK), anthranilic acid, 3-HAA, picolinic acid (PIC), and the excitatory N-methyl-D-aspartate (NMDA) receptor agonist and neurotoxin, quinolinic acid (QUIN) (see FIG. 1). The remaining 5% of tryptophan is metabolised by tryptophan hydroxylase to 5-hydroxytryptophan and then further to 5-hydroxytryptamine (serotonin) and melatonin.

Both the depletion of tryptophan and accumulation of immunosuppressive tryptophan catabolites act to suppress antigen-specific T-cell and natural killer cell responses and induce the formation of regulatory T cells. Because tryptophan catabolism is induced by inflammatory mediators, notably IFN-γ, it is thought to represent an endogenous mechanism that restricts excessive immune responses, thereby preventing immunopathology. However, there is evidence that in disease states this feedback loop may not be beneficial (reviewed in (Munn and Mellor, 2013).

IDO—

The first step of tryptophan catabolism is catalysed by either TDO or IDO. Both enzymes catalyze the oxidative cleavage of the 2,3 double bond in the indole ring, converting tryptophan to N-formylkynurenine. This is the rate-limiting step in tryptophan catabolism by the kynurenine pathway (Grohmann et al., 2003; Stone and Darlington, 2002). TDO is a homotetramer with each monomer having a molecular mass of 48 kDa, whereas IDO has a molecular mass of 45 kDa and a monomeric structure (Sugimoto et al., 2006; Thackray et al., 2008; Zhang et al., 2007). Despite mediating the same reaction, TDO and IDO are structurally distinct, sharing only 10% homology mainly within the active site (Thackray et al., 2008).

IDO is the predominant tryptophan catabolising enzyme extra hepatically and is found in numerous cells, including macrophages, microglia, neurons and astrocytes (Guillemin et al., 2007; Guillemin et al., 2001; Guillemin et al., 2003; Guillemin et al., 2005). IDO transcription is stringently controlled, responding to specific inflammatory mediators. The mouse and human IDO gene promoters contain multiple sequence elements that confer responsiveness to type I (IFN-α/β) and, more potently, type II (IFN-γ) interferons (Chang et al., 2011; Dai and Gupta, 1990; Hassanain et al., 1993; Mellor et al., 2003). Various cell types, including certain myeloid-lineage cells (monocyte-derived macrophages and DCs), fibroblasts, endothelial cells and some tumour-cell lines, express IDO after exposure to IFN-γ (Burke et al., 1995; Hwu et al., 2000; Mellor et al., 2003; Munn et al., 1999; Varga et al., 1996). However, the control of IDO transcription is complex and cell-type specific. IDO activity is found constitutively at the maternal-fetal interface, expressed by human extravillous trophoblast cells (Kudo and Boyd, 2000). Outside of the placenta, functional IDO expression was reported to be highest in the mouse epididymis, gut (distal ileum and colon), lymph nodes, spleen, thymus and lungs (Takikawa et al., 1986).

Another recent variant enzyme of IDO has been shown to catalyse the same enzymatic step: indoleamine-2,3-dioxygenase 2 (IDO2). However, its physiological relevance remains unclear due to its very low activity, the presence of common polymorphisms that inactivate its enzymatic activity in approximately half of all Caucasians and Asians, and the presence of multiple splice variants (Lob et al., 2008; Meininger et al., 2011; Metz et al., 2007).

IDO-deficient mice are at a gross level phenotypical normal (Mellor et al., 2003), however, they are slightly more prone to induction of autoimmunity and stimulation of the innate immune system. IDO−/− knockout mice also display enhanced inflammatory-mediated colon carcinogenesis and exhibit resistance to inflammation-driven lung and skin cancers (Chang et al., 2011; Yan et al., 2010).

Immuno-Modulation:

Tryptophan Depletion and Kynurenine Accumulation-Immunoregulation by tryptophan metabolism modulates the immune system by depletion of the TDO/IDO substrate (tryptophan) in the microenvironment and the accumulation of products such as kynurenine.

Effector T cells are particularly susceptible to low tryptophan concentrations, therefore, depletion of the essential amino acid tryptophan from the local microenvironment resulting in effector T-cell anergy and apoptosis. The depletion of tryptophan is detected by the general control non-derepressible-2 kinase (GCN2) (Munn et al., 2005). The activation of GCN2 triggers a stress-response program that results in cell-cycle arrest, differentiation, adaptation or apoptosis. T cells lacking GCN2 in mice are not susceptible to IDO-mediated anergy by myeloid cells, including dendritic cells in tumor-draining lymph nodes (Munn et al., 2005).

Tryptophan metabolites such as kynurenine, kynurenic acid, 3-hydroxykynurenine, and 3-hydroxy-anthranilic acid suppress T-cell function and are capable of inducing T-cell apoptosis. Recent studies have shown that the aryl hydrocarbon receptor (AHR) is a direct target of kynurenine (Mezrich et al., 2010; Nguyen et al., 2010; Opitz et al., 2011). The AHR is a basic helix-loop-helix Per-Amt-Sim (PAS) family transcription factor. As kynurenine accumulates in a tumour, KYN binds the AHR, translocates to the nucleus and activates transcription of target genes regulated by dioxin-responsive elements (DREs). In T-helper-cells kynurenine results in the generation of regulatory T cells (Treg).

Pharmacological inhibitors of IDO have utility in a wide range of indications, including infectious diseases, cancer, neurological conditions and many other diseases.

Infectious Diseases and Inflammation—

Infection by bacteria, parasites, or viruses induces a strong IFN-γ-dependent inflammatory response. IDO can dampen protective host immunity, thus indirectly leading to increased pathogen burdens. For example, IDO activity attenuates *Toxoplasma gondii* replication in the lung, and the inflammatory damage is significantly decreased by the administration of the IDO inhibitor 1MT after infection (Murakami et al., 2012). Also, in mice infected with murine leukaemia virus (MuLV), IDO was found to be highly expressed, and ablation of IDO enhanced control of viral replication and increased survival (Hoshi et al., 2010). In a model of influenza infection, the immunosuppressive effects of IDO could predispose lungs to secondary bacterial infection (van der Sluijs., et al 2006). In Chagas Disease, which is caused by the *Trypanosoma cruzi* parasite, kynurenine is increased in patients and correlates with disease severity (Maranon et al., 2013). Therefore, IDO inhibitors could be used to improve the outcomes of patients with a wide variety of infectious diseases and inflammatory conditions.

IDO and Immunity to Gut Bacteria—

IDO plays a role in regulating mucosal immunity to the intestinal microbiota. IDO has been shown to regulate commensal induced antibody production in the gut; IDO-deficient mice had elevated baseline levels of immunoglobulin A (IgA) and immunoglobulin G (IgG) in the serum and increased IgA in intestinal secretions. Due to elevated antibody production, IDO deficient mice were more resistant to intestinal colonization by the gram-negative enteric bacterial pathogen *Citrobacter rodentium* than WT mice. IDO-deficient mice also displayed enhanced resistance to the colitis caused by infection with *C. rodentium* (Harrington et al., 2008).

Therefore, pharmacological targeting of IDO activity may represent a new approach to manipulating intestinal immunity and controlling the pathology caused by enteric pathogens including colitis (Harrington et al., 2008).

HIV Infection—

Patients infected with HIV have chronically reduced levels of plasma tryptophan and increased levels of kynurenine, and increased IDO expression (Fuchs et al., 1990 and Zangerle et al., 2002).

In HIV patients the upregulation of IDO acts to suppress immune responses to HIV antigens contributing to the immune evasion of the virus. HIV triggers high levels of IDO expression when it infects human macrophages in vitro (Grant et al., 2000), and simian immunodeficiency virus (SIV) infection of the brain in vivo induces IDO expression by cells of the macrophage lineage (Burudi et al., 2002).

The pathogenesis of HIV is characterized by CD4+ T cell depletion and chronic T cell activation, leading ultimately to AIDS (Douek et al., 2009). CD4+ T helper (TH) cells provide protective immunity and immune regulation through different immune cell functional subsets, including TH1, TH2, T regulatory (Treg), and TH17 cells. Progressive HIV is associated with the loss of TH17 cells and a reciprocal increase in the fraction of the immunosuppressive Treg cells. The loss of TH17/Treg balance is associated with induction of IDO by myeloid antigen-presenting dendritic cells (Favre et al., 2010). In vitro, the loss of TH17/Treg balance is mediated directly by the proximal tryptophan catabolite from IDO metabolism, 3-hydroxyanthranilic acid. Therefore in progressive HIV, induction of IDO contributes to the inversion of the TH17/Treg balance and maintenance of a chronic inflammatory state (Favre et al., 2010). Therefore, IDO inhibitors could have utility in addressing the TH17/Treg balance in HIV.

Sepsis-Induced Hypotension—

Systemic inflammation such as sepsis is characterized by arterial hypotension and systemic inflammatory response syndrome (Riedemann et al., 2003). The associated increase in circulating pro-inflammatory cytokines, including interferon-γ (IFN-γ), leads to the unchecked production of effector molecules such as reactive oxygen and nitrogen species that themselves can contribute to pathology (Riedemann et al., 2003).

The metabolism of tryptophan to kynurenine by IDO expressed in endothelial cells contributes to arterial vessel relaxation and the control of blood pressure (Wang et al., 2010). Infection of mice with malarial parasites (*Plasmodium berghei*), and experimental induction of endotoxemia, caused endothelial expression of IDO, resulting in decreased plasma tryptophan, increased kynurenine, and hypotension. Pharmacological inhibition of IDO increased blood pressure in systemically inflamed mice, but not in mice deficient for IDO or interferon-γ, which is required for IDO induction. Arterial relaxation by kynurenine was mediated by activation of the adenylate and soluble guanylate cyclase pathways. (Wang et al., 2010). Therefore, inhibitors of IDO could have utility in treating sepsis-induced hypotension.

CNS Disorders—

In the central nervous system both fates of TRP which act as a precursor to kynurenine and serotonin are pathways of interest and importance. Metabolites produced by the kynurenine pathway have been implicated to play a role in the pathomechanism of neuroinflammatory and neurodegenerative disorder (summarised in FIG. 2). The first stable intermediate from the kynurenine pathway is KYN. Subsequently, several neuroactive intermediates are generated. They include kynurenic acid (KYNA), 3-hydroxykynurenine (3-HK), and quinolinic acid (QUIN), 3-HK and QUIN are neurotoxic by distinct mechanisms; 3-HK is a potent free-radical generator (Hiraku et al., 1995; Ishii et al., 1992; Thevandavakkam et al., 2010), whereas QUIN is an excitotoxic N-methyl-D-aspartate (NMDA) receptor agonist (Schwarcz et al., 1983; Stone and Perkins, 1981). KYNA, on the other hand, has neuroprotective properties as an antagonist of excitatory amino acid receptors and a free-radical scavenger (Carpenedo et al., 2001; Foster et al., 1984; Goda et al., 1999; Vecsei and Beal, 1990). Changes in the concentration levels of kynurenines can shift the balance to pathological conditions. The ability to influence the metabolism towards the neuroprotective branch of the kynurenine pathway, i.e. towards kynurenic acid (KYNA) synthesis, may be one option in preventing neurodegenerative diseases.

In the CNS, the kynurenine pathway is present to varying extents in most cell types. Infiltrating macrophages, activated microglia and neurons have the complete repertoire of kynurenine pathway enzymes (Guillemin et al., 2000; Lim et al., 2007).

Given the role of IDO in the pathogenesis of several CNS disorders, IDO inhibitors could be used to improve the outcomes of patients with a wide variety of CNS diseases and neurodegeneration.

Amyotrophic Lateral Sclerosis—

Amyotrophic lateral sclerosis (ALS), or Lou Gehrig's disease, is a progressive and fatal neurodegenerative disease targeting the motor system. ALS results in the selective attacking and destruction of motor neurons in the motor cortex, brainstem and spinal cord.

Although multiple mechanisms are likely to contribute to ALS, the kynurenine pathway activated during neuroinflammation is emerging as a contributing factor. Initial inflammation may inflict a nonlethal injury to motor neurons of individuals with a susceptible genetic constitution, in turn triggering a progressive inflammatory process which activates microglia to produce neurotoxic kynurenine metabolites that further destroy motor neurons.

In the brain and spinal cord of ALS patients large numbers of activated microglia, reactive astrocytes, T cells and infiltrating macrophages have been observed (Graves et al., 2004; Henkel et al., 2004). These cells release inflammatory and neurotoxic mediators, among others IFN-γ, the most potent inducer of IDO (McGeer and McGeer 2002). The neuronal and microglial expression of IDO is increased in ALS motor cortex and spinal cord (Chen et al., 2010). It has been proposed that the release of immune activating agents activates the rate-limiting enzyme of the KP, IDO, which generates metabolites such as the neurotoxin QUIN. Therefore, inhibition of IDO would reduce the synthesis of neurotoxic QUIN, which has been clearly implicated in the pathogenesis of ALS.

Huntington's Disease—

Huntington's disease (HD) is a genetic autosomal dominant neurodegenerative disorder caused by expansion of the CAG repeats in the huntingtin (htt) gene. Patients affected by HD display progressive motor dysfunctions characterized by abnormality of voluntary and involuntary movements (choreoathetosis) and psychiatric and cognitive disturbances. In-life monitoring of metabolites with in the KYN pathway provide one of the few biomarkers that correlates with the number of CAG repeats and hence the severity of the disorder (Forrest et al., 2010). Post mortem very high levels of QUIN are found located in areas of neurodegeneration, while striatal glutamatergic neurones, on which QUIN acts as an excitotoxin, are a principal class lost in the disease.

Alzheimer's Disease—

Alzheimer's disease (AD) is an age-related neurodegenerative disorder characterised by neuronal loss and dementia. The histopathology of the disease is manifested by the accumulation of intracellular β-amyloid (Aβ) and subsequent formation of neuritic plaques as well as the presence of neurofibrillary tangles in specific brain regions associated with learning and memory. The pathological mechanisms underlying this disease are still controversial, however, there is growing evidence implicating KP metabolites in the development and progression of AD.

It has been shown that Aβ (1-42) can activate primary cultured microglia and induce IDO expression (Guillemin et al., 2003; Walker et al., 2006). Furthermore, IDO overexpression and increased production of QUIN have been observed in microglia associated with the amyloid plaques in the brain of AD patients (Guillemin et al., 2005). QUIN has been shown to lead to tau hyperphosphorylation in human cortical neurons (Rahman et al., 2009). Thus, overexpression of IDO and over-activation of the KP in microglia are implicated in the pathogenesis of AD.

Psychiatric Disorders and Pain—

Most tryptophan is processed through the kynurenine pathway. A small proportion of tryptophan is processed to 5-HT and hence to melatonin, both of which are also substrates for IDO. It has long been known that amongst other effects acute tryptophan depletion can trigger a depressive episode and produces a profound change in mood even in healthy individuals. These observations link well with the clinical benefits of serotonergic drugs both to enhance mood and stimulate neurogenesis.

The co-morbidity of depressive symptoms and implication of the kynurenine pathway in inflammation also implicate a role in the treatment of chronic pain (Stone and Darlington 2013).

Schizophrenic patients exhibit elevated KYN levels both in CSF and brain tissue, particularly the frontal cortex. This has been associated with the "hypofrontality" observed in schizophrenia. Indeed rodents treated with neuroleptics show a marked reduction in frontal KYN levels. These changes have been associated with reduced KMO and 3HAO. Evidence includes an association between a KMO polymorphism, elevated CSF KYN and schizophrenia (Holtze et. al., 2012). Taken together there is potential for manipulations in this pathway to be both pro-cognate and neuroleptic.

Pain and depression are frequently comorbid disorders. It has been shown that IDO1 plays a key role in this comorbidity. Recent studies have shown that IDO activity is linked to (a) decreased serotonin content and depression (Dantzer et al., 2008; Sullivan et al., 1992) and (b) increased kynurenine content and neuroplastic changes through the effect of its derivatives such as quinolinic acid on glutamate receptors (Heyes et al., 1992).

In rats chronic pain induced depressive behaviour and IDO upregulation in the bilateral hippocampus. Upregulation of IDO resulted in the increased kynurenine/tryptophan ratio and decreased serotonin/tryptophan ratio in the bilateral hippocampus. Furthermore, IDO gene knockout or pharmacological inhibition of hippocampal IDO activity attenuated both nociceptive and depressive behaviour (Kim et al., 2012).

Since proinflammatory cytokines have been implicated in the pathophysiology of both pain and depression, the regulation of brain IDO by proinflammatory cytokines serves as a critical mechanistic link in the comorbid relationship between pain and depression through the regulation of tryptophan metabolism.

Multiple Sclerosis—

Multiple sclerosis (MS) is an autoimmune disease characterized by inflammatory lesions in the white matter of the nervous system, consisting of a specific immune response to the myelin sheet resulting in inflammation and axonal loss (Trapp et al., 1999; Owens, 2003).

Accumulation of neurotoxic kynurenine metabolites caused by the activation of the immune system is implicated in the pathogenesis of MS. QUIN was found to be selectively elevated in the spinal cords of rats with EAE, an autoimmune animal model of MS (Flanagan et al., 1995). The origin of the increased QUIN in EAE was suggested to be the macrophages. QUIN is an initiator of lipid peroxidation and high local levels of QUIN near myelin may contribute to the demyelination in EAE and possibly MS.

Interferon beta 1b (IFN-β1b) induces KP metabolism in macrophages at concentrations comparable to those found in the sera of IFN-b treated patients, this which may be a limiting factor in its efficacy in the treatment of MS (Guillemin et al., 2001). After IFN-β administration, increased kynurenine levels and kynurenine/tryptophan ratio were found in the plasma of MS patients receiving IFN-b injection compared to healthy subjects indicating an induction of IDO by IFN-β (Amirkhani et al., 2005). IFN-β1b, leads to production of QUIN at concentrations sufficient to disturb the ability of neuronal dendrites to integrate incoming signals and kill oligodendrocytes (Cammer 2001). In IFN-β1b-treated patients concomitant blockade of the KP with an IDO inhibitor may improve its efficacy of IFN-β1b.

Parkinson's Disease—

Parkinson's disease (PD) is a common neurodegenerative disorder characterised by loss of dopaminergic neurons and localized neuroinflammation.

Parkinson's disease is associated with chronic activation of microglia (Gao and Hong, 2008). Microglia activation release neurotoxic substances including reactive oxygen species (ROS) and proinflammatory cytokines such as IFN-γ (Block et al., 2007), a potent activator of KP via induction of IDO expression. KP in activated microglia leads to upregulation of 3HK and QUIN, 3HK is toxic primarily as a result of conversion to ROS (Okuda et al., 1998). The combined effects of ROS and NMDA receptor-mediated excitotoxicity by QUIN contribute to the dysfunction of neurons and their death (Braidy et al., 2009; Stone and Perkins, 1981). However, picolinic acid (PIC) produced through KP activation in neurons, has the ability to protect neurons against QUIN-induced neurotoxicity, being NMDA agonist (Jhamandas et al., 1990). Microglia can become overactivated, by proinflammatory mediators and stimuli from dying neurons and cause perpetuating cycle of further microglia activation microgliosis. Excessive microgliosis will cause neurotoxicity to neighbouring neurons and resulting in neuronal death, contributing to progression of Parkinson's disease. (Zinger et al 2011)

Therefore, PD is associated with an imbalance between the two main branches of the KP within the brain. KYNA synthesis by astrocytes is decreased and concomitantly, QUIN production by microglia is increased.

HIV—

HIV patients, particularly those with HIV-linked dementia (Kandanearatchi & Brew 2012), often have significantly elevated KYN levels in CSF. These levels are directly related to the development of neurocognitive decline and often the presence of sever psychotic symptoms (Stone & Darlington 2013).

Cancer—

It is clear that tumours can induce tolerance to their own antigens. Tryptophan catabolism in cancer is increasingly being recognized as an important micro-environmental factor that suppresses antitumour immune responses. Depletion of tryptophan and accumulation of immunosuppressive tryptophan catabolites such as kynurenine create an immunosuppressive milieu in tumours and in tumour-draining lymph nodes by inducing T-cell anergy and apoptosis. Such immunosuppression in the tumour microenvironment may help cancers evade the immune response and enhance tumorigenicity (reviewed in Adam et al., 2012).

Recently, IDO has been implicated in tumour progression. IDO has been found to be overexpressed in various cancers. IDO mediates immunosuppressive effects through the metabolization of Trp to kynurenine, triggering downstream signalling through GCN2, mTOR and AHR that can affect differentiation and proliferation of T cells. Also, expression of IDO by activated dendritic cells can serve to activate regulatory T cells (Tregs) and inhibit tumor-specific effector CD8+ T cells, thereby constituting a mechanism by which the immune system can restrict excessive lymphocyte reactivity (reviewed in Platten et al., 2012).

IDO—

Increased expression of IDO has been shown to be an independent prognostic variable for reduced survival in patients with acute myeloid leukemia (AML), small-cell lung, melanoma, ovarian, colorectal, pancreatic, and endometrial cancers (Okamoto et al., 2005; Ino et al., 2006). Indeed, sera from cancer patients have higher kynurenine/tryptophan ratios than sera from normal volunteers (Liu et al., 2010; Weinlich et al., 2007; Huang et al., 2002). The level of IDO expression was also shown to correlate with the number of tumour infiltrating lymphocytes in colorectal carcinoma patients (Brandacher et al., 2006).

In preclinical models, transfection of immunogenic tumour cells with recombinant IDO prevented their rejection in mice (Uyttenhove et al., 2003). While, ablation of IDO expression led to a decrease in the incidence and growth of 7,12-dimethylbenz(a)anthracene-induced premalignant skin papillomas (Muller et al., 2008). Moreover. IDO inhibition slows tumour growth and restores anti-tumour immunity (Koblish et al., 2010) and IDO inhibition synergises with cytotoxic agents, vaccines and cytokines to induce potent anti-tumour activity (Uyttenhove et al., 2003; Muller et al., 2005; Zeng et al., 2009).

Inhibition of IDO will dramatically lower kynurenine levels, relieving the brake on the immune system allowing it to attack and eliminate tumours. While there is evidence that an IDO inhibitor would be useful as a stand-alone agent, inhibitors of this type would be particularly effective when used in combination with other cancer immunotherapies. In fact, upregulation of IDO expression has been identified as a mechanism by which tumours gain resistance to the CTLA-4 blocking antibody ipilimumab. Ipilimumab blocks the co-stimulatory molecule CTLA-4, causing tumour-specific T cells to remain in an activated state. IDO knockout mice treated with anti-CTLA-4 antibody demonstrate a striking delay in B16 melanoma tumor growth and increased overall survival when compared with wild-type mice. Also, CTLA-4 blockade strongly synergizes with IDO inhibitors to mediate tumour rejection. Similar data was also reported for IDO inhibitors in combination with anti-PD1 and anti-PDL-1 antibodies (Holmgaard et al., 2013).

Agents that will influence an immunosuppressive environment may also be relevant to chimeric antigen receptor T cell therapy (CAR-T) therapies to enhance efficacy and patient responses.

Other Diseases—

Although these effects are defensive strategies to cope with infection and inflammation, they may have unintended consequences because kynurenines formed during IDO mediated degradation of tryptophan can chemically modify proteins and have been shown to be cytotoxic (Morita et al., 2001; Okuda et al., 1998). In coronary heart disease, inflammation and immune activation are associated with increased blood levels of kynurenine (Wirleitner et al., 2003) possibly via interferon-γ-mediated activation of IDO. In experimental chronic renal failure, activation of IDO leads to increased blood levels of kynurenines (Tankiewicz et al., 2003), and in uremic patients kynurenine-modified proteins are present in urine (Sala et al., 2004). Further, renal IDO expression may be deleterious during inflammation, because it enhances tubular cell injury.

General anaesthesia unfortunately mimics many of these effects inducing stress and inflammatory processes. Post anaesthesia cognitive dysfunction has often been correlated with these sequelae. Recently these deficits have been shown to be correlated with changes in kynurenine pathway markers, but not cytokines, following cardiac surgery and in recovering stroke patients (Stone and Darlington 2013).

Cataracts—

A cataract is a clouding of the lens inside the eye that leads to a decrease in vision. Recent studies suggest that kynurenines might chemically alter protein structure in the human lens leading to cataract formation. In the human lens IDO activity is present mainly in the anterior epithelium (Takikawa et al., 1999). Several kynurenines, such as kynurenine (KYN), 3-hydroxykynurenine (3OHKYN), and 3-hydroxykynurenine glucoside (3OHKG) have been detected in the lens; where they were thought to protect the retina by absorbing UV light and therefore are commonly referred to as UV filters. However, several recent studies show that kynurenines are prone to deamination and oxidation to form α,β-unsaturated ketones that chemically react and modify lens proteins (Taylor et al., 2002). Kynurenine mediated modification could contribute to the lens protein modifications during aging and cataractogenesis. They may also reduce the chaperone function of α-crystallin, which is necessary for maintaining lens transparency.

Transgenic mouse lines that overexpress human IDO in the lens developed bilateral cataracts within 3 months of birth. It was demonstrated that IDO-mediated production of kynurenines results in defects in fibre cell differentiation and their apoptosis (Mailankot et al., 2009). Therefore inhibition of IDO may slow the progression of cataract formation.

Endometriosis—

Endometriosis, the presence of endometrium outside the uterine cavity, is a common gynaecological disorder, causing abdominal pain, dyspareunia and infertility. IDO expression was found to be higher in eutopic endometrium from women with endometriosis by microarray analysis (Burney et al., 2007 and Aghajanova et al., 2011). Furthermore, IDO was shown to enhance the survival and invasiveness of endometrial stromal cells (Mei et al., 2013). Therefore, an IDO inhibitor could be used as a treatment for endometriosis.

Contraception and Abortion—

The process of implantation of an embryo requires mechanisms that prevent allograft rejection; and tolerance to the fetal allograft represents an important mechanism for maintaining a pregnancy. Cells expressing IDO in the foeto-maternal interface protect the allogeneic foetus from lethal rejection by maternal immune responses. Inhibition of IDO by exposure of pregnant mice to 1-methyl-tryptophan induced a T cell-mediated rejection of allogeneic concepti, whereas syngeneic concepti were not affected; this suggests that IDO expression at the foetal-maternal interface is necessary to prevent rejection of the foetal allograft (Munn et al., 1998). Accumulating evidence indicates that IDO production and normal function at the foetal-maternal interface may play a prominent role in pregnancy tolerance (Durr and Kindler., 2013). Therefore, an IDO inhibitor could be used as a contraceptive or abortive agent.

On the above basis, the inventors have determined that a strong rationale exists for the therapeutic utility of drugs which block the activity of IDO, in treating the above-mentioned diseases, conditions and disorders.

Having regard to the above, it is an aim of the present invention to provide IDO inhibitors, and in particular IDO inhibitors for use in medicine. It is a further aim to provide pharmaceutical compositions comprising such inhibitors, and in particular to provide compounds and pharmaceutical compositions for treating a cancer, an inflammatory condition, an infectious disease, a central nervous system disease or disorder and other diseases, conditions and disorders. It is also an aim to provide methods of synthesis of the compounds.

WO 2012/084971 discloses indole amide compounds with substitution patterns which are different to those presently envisaged. These compounds are disclosed as being direct antibacterial agents. IDO inhibition is not mentioned, and there is no disclosure that the compounds have IDO inhibitory activity, or a pharmacology associated with an IDO mechanism.

WO 94/19321 and WO 2014/009794 each disclose compounds for treating HIV. The most similar compounds are indole amides with substitution patterns which are different to those presently envisaged. In WO 94/19321 the compounds are indicated to be direct reverse transcriptase inhibitors, whilst in WO 2014/009794 they are indicated to be direct anti-virals. IDO inhibition is not mentioned, and there is no disclosure that the compounds have IDO inhibitory activity, or a pharmacology associated with an IDO mechanism.

WO 2008/002674 and WO 03/035621 disclose protein kinase and phosphatase inhibitors, which may be employed inter alia in the treatment of cancer. Some such compounds are indole amides with substitution patterns different to those investigated by the present inventors. IDO inhibition is not mentioned, and there is no disclosure that the compounds have IDO inhibitory activity, or a pharmacology associated with an IDO mechanism, i.e. the ablation of tryptophan depletion/kynurenine production, with the associated increase in T-cell proliferation and tumour immune response.

Previously, Dolusic et al. have tested indole compounds to determine their IDO inhibitory activity (European Journal of Medicinal Chemistry 46 (2011) 3058-3065; Bioorganic and Medicinal Chemistry, Vol. 19(4), 2011, pp 1550-1561). That study determined that certain indole compounds with ketone substituents at the 2-position might be useful IDO inhibitors. However, the activity of such compounds was found to be marginal at best. It was concluded that an amide compound of the type the inventors have investigated was not an effective inhibitor as compared with the ketone compounds. However, the inventors have now determined that Dolusic et al. were mistaken about such amide compounds in that certain variants are highly active.

SUMMARY OF THE INVENTION

Disclosed herein are compounds having formula (I):

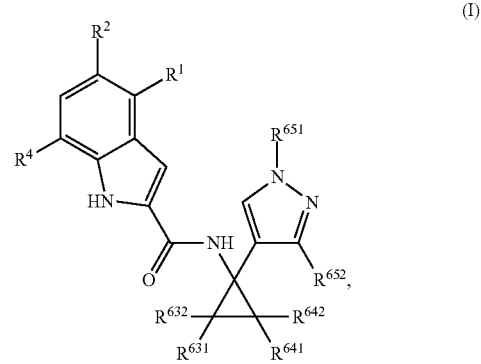

wherein $R^2$ is selected from —Cl, —Br and —CN; $R^1$ and $R^4$ are independently selected from —H and —F; $R^{631}$, $R^{632}$, $R^{641}$ and $R^{642}$ are independently selected from —H, —F and substituted or unsubstituted $C_1$-$C_3$ alkyl groups; and $R^{651}$ and $R^{652}$ are independently selected from —H and substituted or unsubstituted $C_1$-$C_3$ alkyl groups and substituted or unsubstituted phenyl groups; and wherein at least one of $R^{631}$, $R^{632}$, $R^{641}$, $R^{642}$ and $R^{652}$ is not —H, or wherein when all of $R^{631}$, $R^{632}$, $R^{641}$, $R^{642}$ and $R^{652}$ are —H, $R^{651}$ is not Me or Et.

DETAILED DESCRIPTION OF THE INVENTION

Figure 1:
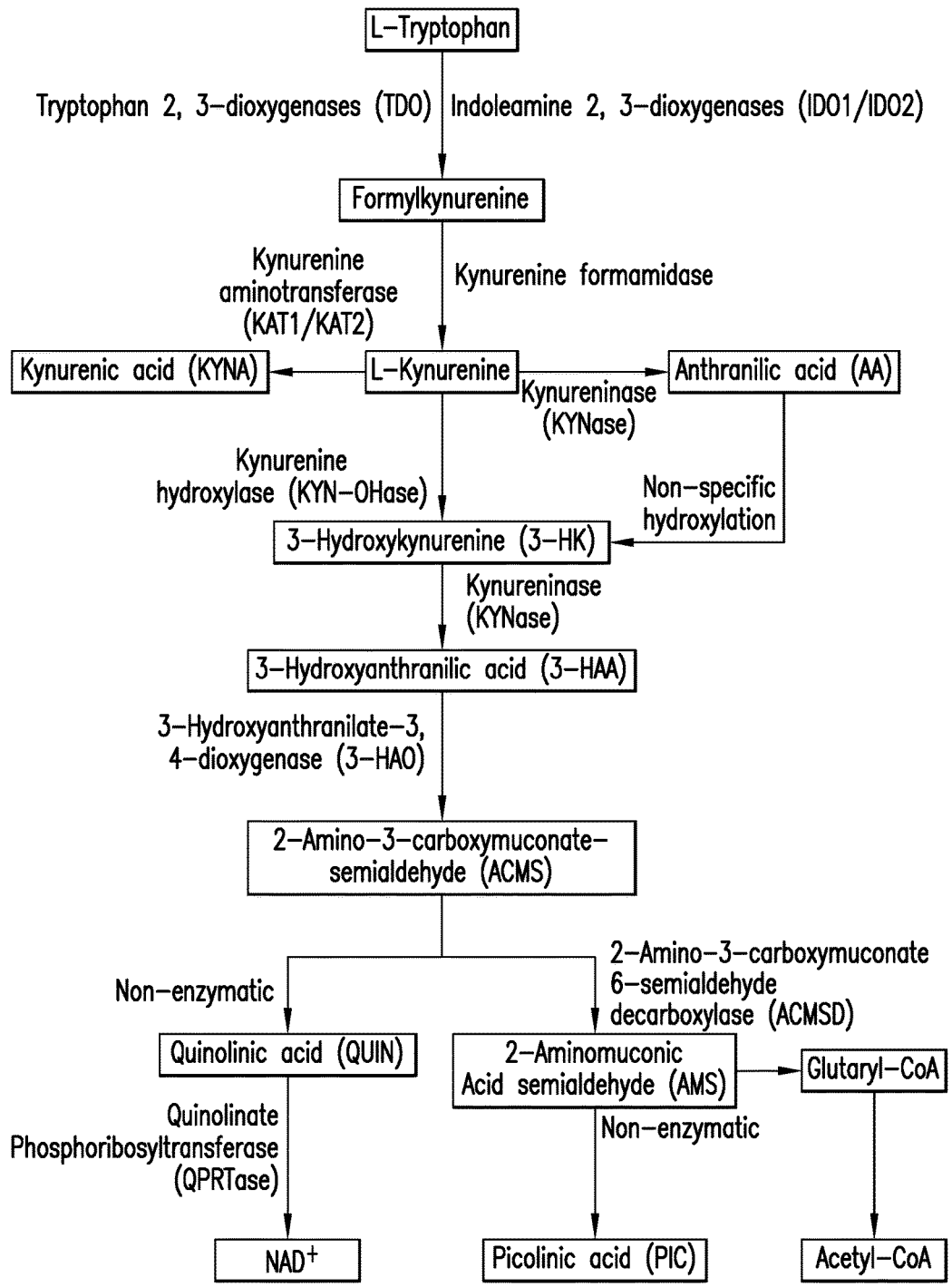
FIG. 1 shows a schematic diagram of tryptophan catabolism along the KP (from "The Kynurenine Pathway in Brain Tumour Pathogenesis", Adam et al., 2012, Cancer Res 72:5649-57).
Figure 2:
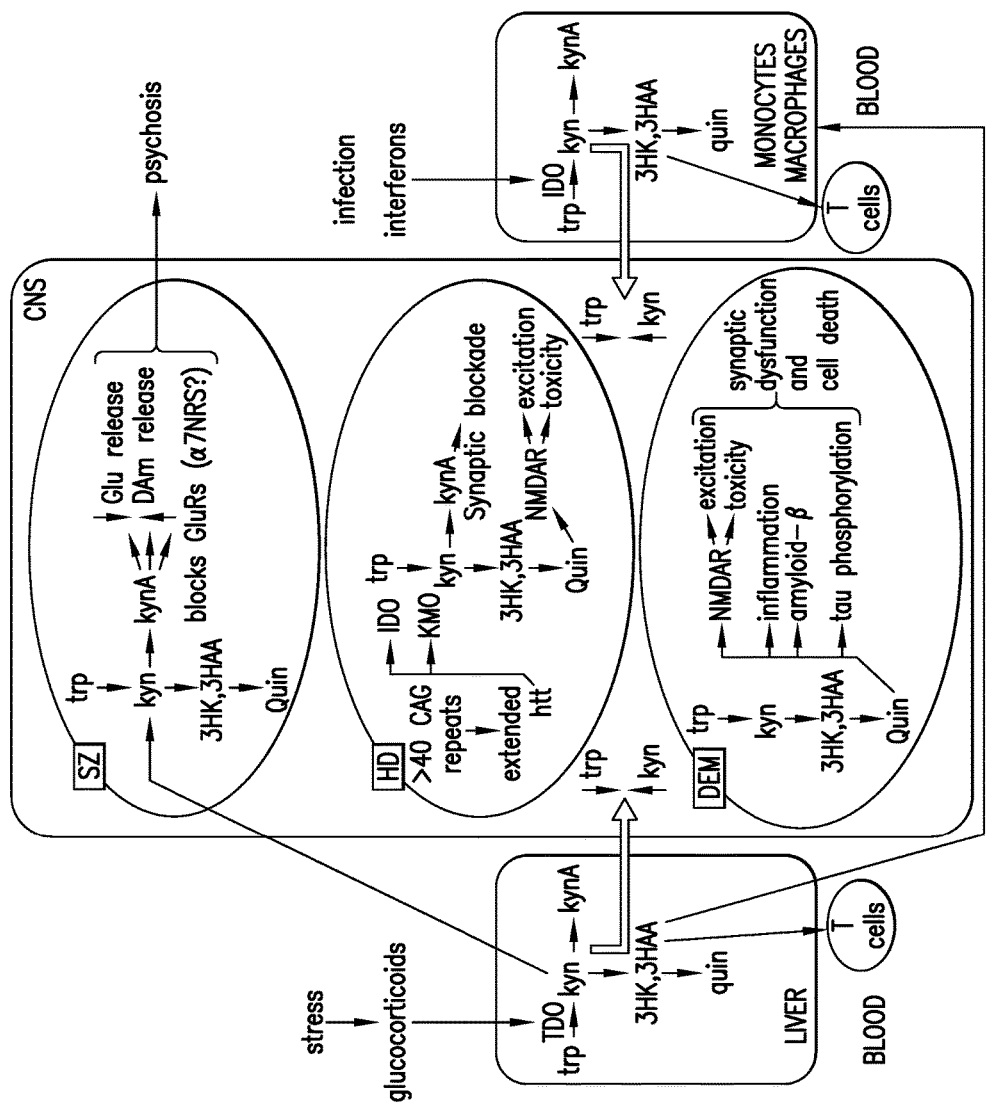
FIG. 2 shows a schematic summary of the involvement of kynurenine in CNS disorders (from "The kynurenine pathway as a therapeutic target in cognitive and neurodegenerative disorders", Stone and Darlington. Br. J. Pharmacol. 2013 169(6): 1211-27.

It has now been determined that compounds having formula (I) shown above have strong IDO inhibitory activity. Such compounds have significant potential for use in medicine. Thus, the compounds may be used as IDO inhibitors, such as for treating any disease associated with an IDO mechanism. Typical diseases associated with an IDO mechanism are described above and below herein, and the invention therefore extends to compounds for use in treating such diseases.

In the present context, $R^1$ and $R^4$ may be the same or different since they are selected independently. In typical embodiments, both of $R^1$ and $R^4$ are —H. In other typical embodiments $R^1$ is —F and $R^4$ is —H, or $R^1$ is —H and $R^4$ is —F, or $R^1$ is —F and $R^4$ is —F. In one embodiment, both of $R^1$ and $R^4$ are —H or one of $R^1$ and $R^4$ is —F and the other is —H, although in some less typical embodiments both of $R^1$ and $R^4$ may be —F.

$R^{631}$, $R^{632}$, $R^{641}$ and $R^{642}$ may be the same or different since they are selected independently. In typical embodiments at least one of $R^{631}$, $R^{632}$, $R^{641}$ and $R^{642}$ is not —H. In other embodiments two or more, three or more, or all of $R^{631}$, $R^{632}$, $R^{641}$ and $R^{642}$ are not —H. In one embodiment, $R^{641}$ and/or $R^{642}$ is not —H. In one embodiment, $R^{642}$ is not —H. However, other embodiments in which all of $R^{631}$, $R^{632}$, $R^{641}$ and $R^{642}$ are —H are not excluded. When one or more of $R^{631}$, $R^{632}$, $R^{641}$ and $R^{642}$ is a substituted or unsubstituted $C_1$-$C_3$ alkyl group, the $C_1$-$C_3$ alkyl group may typically be selected from methyl (Me), ethyl (Et), propyl (Pr) and iso-propyl (i-Pr) groups. When the $C_1$-$C_3$ alkyl group is a substituted $C_1$-$C_3$ alkyl group it may typically be selected from alkyl groups with fluorine substituents, such as —$CH_2F$, —$CHF_2$, and —$CF_3$.

$R^{651}$ and $R^{652}$ may be the same or different since they are selected independently. In typical embodiments at least one of $R^{651}$ and $R^{652}$ is not —H. In yet other typical embodiments both of $R^{651}$ and $R^{652}$ are not —H. However, other embodiments in which both of $R^{651}$ and $R^{652}$ are —H are not excluded. When one or both of $R^{651}$ and $R^{652}$ is a substituted or unsubstituted $C_1$-$C_3$ alkyl group, the $C_1$-$C_3$ alkyl group may typically be selected from methyl (Me), ethyl (Et), propyl (Pr) and iso-propyl (i-Pr) groups. When the $C_1$-$C_3$ alkyl group is a substituted $C_1$-$C_3$ alkyl group it may typically be selected from alkyl groups with fluorine substituents, such as —$CH_2F$, —$CHF_2$, and —$CF_3$. When one or both of $R^{651}$ and $R^{652}$ is a substituted or unsubstituted phenyl group, typically the phenyl group is unsubstituted, i.e. is -Ph. In one embodiment, if one of these groups is a phenyl group, $R^{651}$ is phenyl rather than $R^{652}$.

In the formulae herein, all tautomeric forms of the ring system (including the tautomeric forms of the 6-membered ring and the tautomeric forms of the 5-membered ring are intended to be included. Additionally in the formulae herein, where stereochemistry is not explicitly indicated, all stereoisomers of the formulae are intended to be included, including enantiomers, cis-trans isomers, meso-compounds and the like. Thus, where no stereochemistry is given at a chiral centre the invention also includes both isolated enantiomers and the racemic mixture. Thus, the compounds of the present invention extend to isolated enantiomers, and/or a mixture of two or more enantiomers, and/or a mixture of two or more diastereomers (e.g. where there is more than one chiral centre), and/or a mixture of two or more epimers, and/or racemic mixtures.

In the present context, in some embodiments any of $R^{631}$, $R^{632}$, $R^{641}$ and $R^{642}$ may form a ring with any other of $R^{631}$, $R^{632}$, $R^{641}$ and $R^{642}$. In one embodiment, no ring is formed. Thus, in some embodiments the following substituents may together form a ring: $R^{631}$ and $R^{632}$, $R^{631}$ and $R^{641}$, $R^{631}$ and $R^{642}$, $R^{632}$ and $R^{641}$, $R^{632}$ and $R^{642}$, and $R^{641}$ and $R^{642}$. In one embodiment, R groups attached to the same atom do not together form a ring, although this is not excluded.

In the context of the present invention, a compound is considered to be an IDO inhibitor if its presence is capable of preventing, reducing or slowing the conversion of tryptophan into N-formylkynurenine by IDO as compared to the same conversion in its absence. In one embodiment, a compound is considered to be an IDO inhibitor if its inhibitory activity shows a pIC50 value of 4.50 or more in the SKOV-3 ovary adenocarcinoma cell-based assay as set out in the Examples. Typically the compounds of the present invention have such a pIC50 value greater than that of compound REF 1 and further typically the compounds of the present invention have such a pIC50 value greater than 7.00.

In all of the embodiments of this invention (both above and below herein), unless otherwise specified, when an R group is a substituted R group, the substituent is not especially limited, provided that it does not prevent the IDO inhibitory function from occurring. In all of the embodiments mentioned in connection with this invention, both above and in the following, unless otherwise specified, the substituent on a substituted R group may be selected from —H, —F and -Me. In addition, any substituent may comprise a combination of two or more of the substituents defined above.

As has been described, a compound disclosed herein has formula (I):

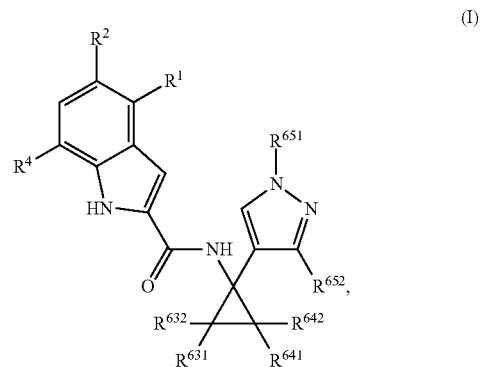

wherein $R^2$ is selected from —Cl, —Br and —CN; $R^1$ and $R^4$ are independently selected from —H and —F; $R^{631}$, $R^{632}$, $R^{641}$ and $R^{642}$ are independently selected from —H, —F and substituted or unsubstituted $C_1$-$C_3$ alkyl groups; and $R^{651}$ and $R^{652}$ are independently selected from —H and substituted or unsubstituted $C_1$-$C_3$ alkyl groups and substituted or unsubstituted phenyl groups; and wherein at least one of $R^{631}$, $R^{632}$, $R^{641}$, $R^{642}$ and $R^{652}$ is not —H, or wherein when all of $R^{631}$, $R^{632}$, $R^{641}$, $R^{642}$ and $R^{652}$ are —H, $R^{651}$ is not Me or Et.

Thus, in view of the typical embodiments already described, in certain embodiments the invention relates to a compound as defined above, which compound is a compound of the following formula:

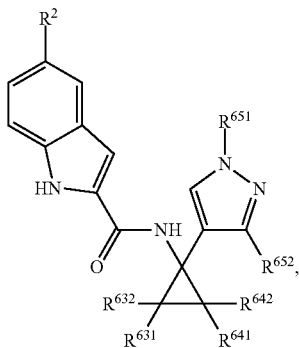

wherein $R^2$, $R^{631}$, $R^{632}$, $R^{641}$, $R^{642}$, $R^{651}$ and $R^{652}$ have the same meanings described above and herein, and wherein at least one of $R^{631}$, $R^{632}$, $R^{641}$, $R^{642}$ and $R^{652}$ is not —H, or wherein when all of $R^{631}$, $R^{632}$, $R^{641}$, $R^{642}$ and $R^{652}$ are —H, $R^{651}$ is not -Me or -Et.

Further in view of the typical embodiments already described, in certain embodiments the invention relates to a compound as defined above, which compound is a compound of the following formula:

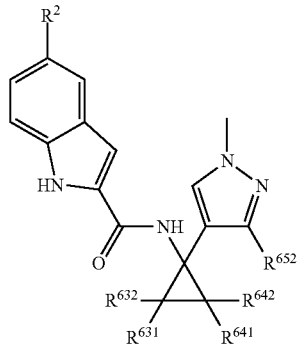

wherein $R^2$, $R^{631}$, $R^{632}$, $R^{641}$, $R^{642}$ and $R^{652}$ have the same meanings described above and herein, and wherein at least one of $R^{631}$, $R^{632}$, $R^{641}$, $R^{642}$ and $R^{652}$ is not —H.

Further in view of the typical embodiments already described, in certain embodiments the invention relates to a compound as defined above, which compound is a compound of the following formula:

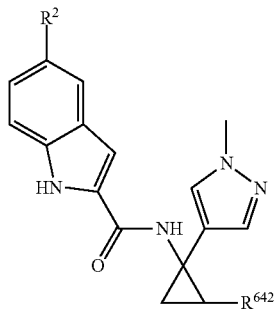

wherein $R^2$ and $R^{642}$ have the same meanings described above and herein, and wherein $R^{642}$ is not —H. In one embodiment, $R^2$ is —Br and/or $R^{642}$ is $C_1$-$C_3$ alkyl. In another embodiment, $R^2$ is —Cl and/or $R^{642}$ is $C_1$-$C_3$ alkyl. In another embodiment, $R^2$ is —CN and/or $R^{642}$ is $C_1$-$C_3$ alkyl. In one embodiment, $R^2$ is —Br and $R^{642}$ is methyl. In another embodiment, $R^2$ is —Cl and $R^{642}$ is methyl. In another embodiment, $R^2$ is —CN and $R^{642}$ is methyl.

In one embodiment, a compound is selected from:

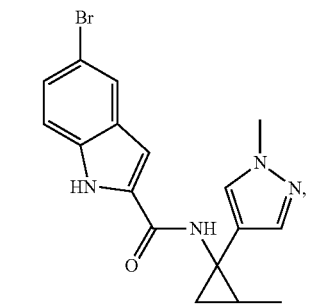

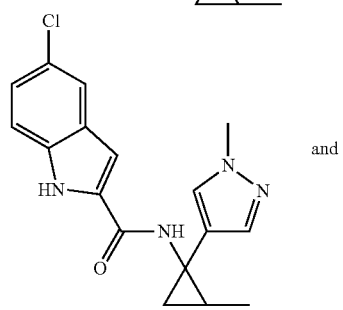

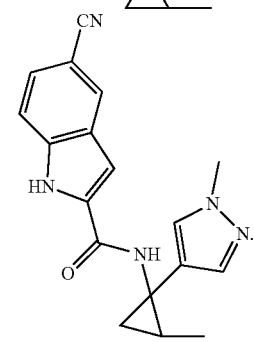

As has been mentioned any of the present compounds herein, when depicted without indicating stereochemistry, are intended to include all possible stereochemical variations of the compounds. Thus, the compounds depicted above and below herein include all possible isolated enantiomers (including all possible isolated (+) enantiomers and all possible isolated (−) enantiomers), all possible isolated cis isomers and all possible isolated trans isomers, and all possible meso-compounds, and the like. The invention also includes all possible mixtures of enantiomers in any proportions, and all possible racemic mixtures. Thus, the compounds of the present invention extend to a mixture of two or more enantiomers, and/or a mixture of two or more diastereomers (e.g. where there is more than one chiral centre), and/or a mixture of two or more epimers.

In more typical embodiments, specific stereochemistries are preferred. Thus, isolated trans isomers (trans across the cyclopropane ring) of the compounds herein are preferred. In certain more specific cases isolated (+) enantiomers of the compounds herein are preferred.

Thus, in typical embodiments of the invention, compounds in which the indole-containing group on the cyclopropyl ring is trans to the sterically largest of the $R^{631}$, $R^{632}$, $R^{641}$ and $R^{642}$ groups are particularly preferred. More preferably in such compounds the sterically largest of the $R^{631}$, $R^{632}$, $R^{641}$ and $R^{642}$ groups is the $R^{642}$ group, and thus in such cases more preferably the indole-containing group on the cyclopropyl ring is trans to the $R^{642}$ group. Furthermore, the (+) enantiomers of such compounds are preferred, although the (−) enantiomers, the racemates, and mixtures of enantiomers in any proportion are also included. Nevertheless, compounds in which the indole-containing group on the cyclopropyl ring is cis to the sterically largest of the $R^{631}$, $R^{632}$, $R^{641}$ and $R^{642}$ groups are also included. As with trans compounds, in these cis compounds it is also preferred that the $R^{642}$ group is sterically the largest of the $R^{631}$, $R^{632}$, $R^{641}$ and $R^{642}$ groups, such that the indole-containing group on the cyclopropyl ring is cis to the $R^{642}$ group.

Further in view of the typical embodiments already described, in certain embodiments the invention relates to a compound as defined above, which compound is a chiral compound comprising a racemic mixture or an isolated enantiomer having one (an isolated enantiomer) or both (a racemic mixture) of the following formulae:

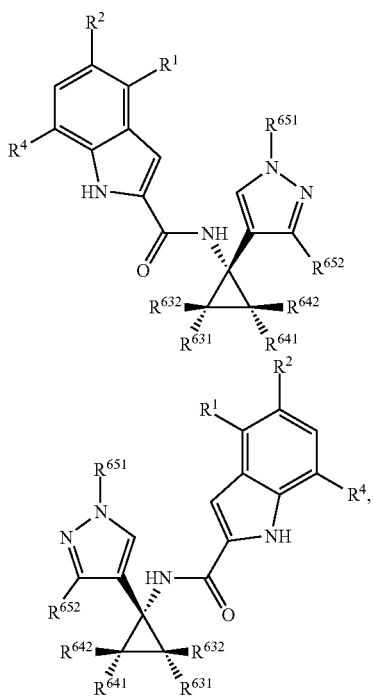

wherein $R^2$ is selected from —Cl, —Br and —CN; $R^1$ and $R^4$ are independently selected from —H and —F; $R^{631}$, $R^{632}$, $R^{641}$ and $R^{642}$ are independently selected from —H, —F and substituted or unsubstituted $C_1$-$C_3$ alkyl groups; and $R^{651}$ and $R^{652}$ are independently selected from —H and substituted or unsubstituted $C_1$-$C_3$ alkyl groups and substituted or unsubstituted phenyl groups; and wherein $R^{642}$ is a sterically larger group than any of $R^{631}$, $R^{632}$ and $R^{641}$.

Thus, in typical embodiments of the invention, the invention relates to a compound as defined above, which compound is a chiral compound comprising a racemic mixture or an isolated enantiomer having one (an isolated enantiomer) or both (a racemic mixture) of the following formulae:

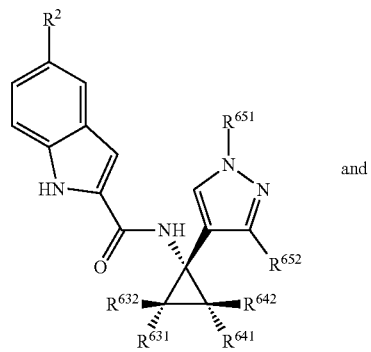

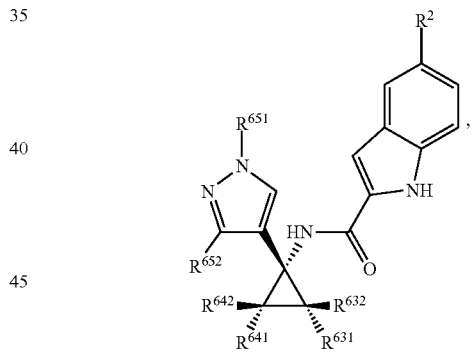

wherein $R^2$ is selected from —Cl, —Br and —CN; $R^{631}$, $R^{632}$, $R^{641}$ and $R^{642}$ are independently selected from —H, —F and substituted or unsubstituted $C_1$-$C_3$ alkyl groups; $R^{651}$ and $R^{652}$ are independently selected from —H and substituted or unsubstituted $C_1$-$C_3$ alkyl groups and substituted or unsubstituted phenyl groups; and wherein $R^{642}$ is a sterically larger group than any of $R^{631}$, $R^{632}$ and $R^{641}$.

In further typical embodiments of the invention, the invention relates to a compound as defined above, which compound is a chiral compound comprising a racemic mixture or an isolated enantiomer having one (an isolated enantiomer) or both (a racemic mixture) of the following formulae:

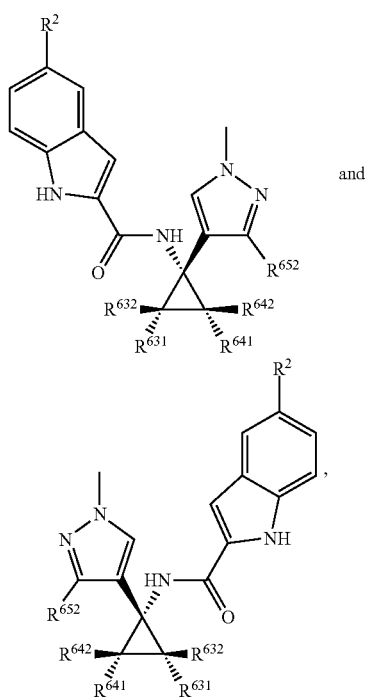

wherein $R^2$ is selected from —Cl, —Br and —CN; $R^{631}$, $R^{632}$, $R^{641}$ and $R^{642}$ are independently selected from —H, —F and substituted or unsubstituted $C_1$-$C_3$ alkyl groups; $R^{652}$ is selected from —H and substituted or unsubstituted $C_1$-$C_3$ alkyl groups and substituted or unsubstituted phenyl groups; and wherein $R^{642}$ is a sterically larger group than any of $R^{631}$, $R^{632}$ and $R^{641}$.

In further typical embodiments of the invention, the invention relates to a compound as defined above, which compound is a chiral compound comprising a racemic mixture or an isolated enantiomer having one (an isolated enantiomer) or both (a racemic mixture) of the following formulae:

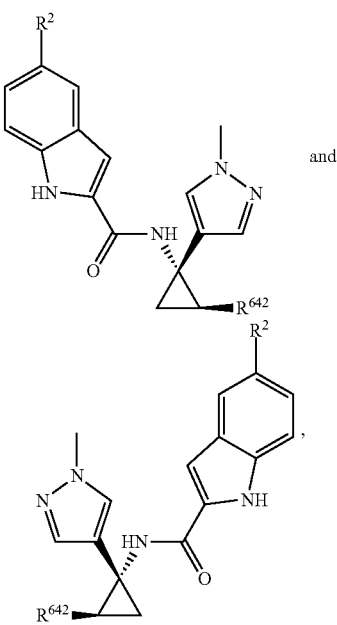

wherein $R^2$ is selected from —Cl, —Br and —CN; and wherein $R^{642}$ is independently selected from —F and substituted or unsubstituted $C_1$-$C_3$ alkyl groups. Isolated (+) enantiomers of such compounds are preferred.

Thus, in typical embodiments of the invention, isolated enantiomers and racemic mixtures of the following chiral compounds are especially preferred:

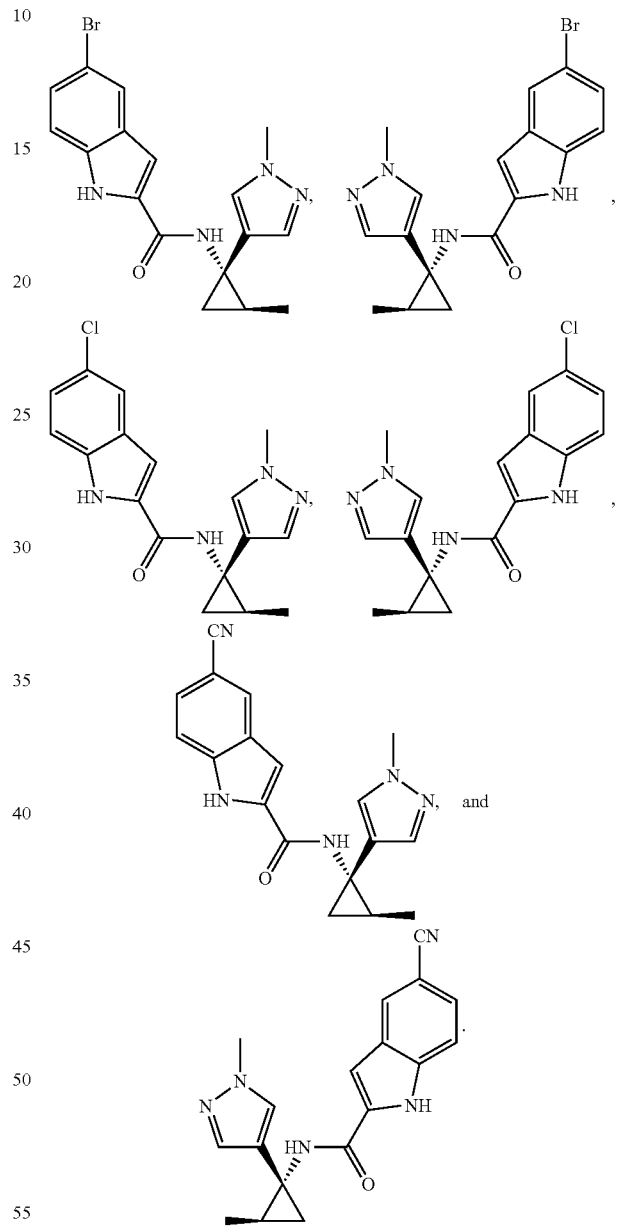

As mentioned above, isolated (+) enantiomers of such compounds are particularly preferred.

In alternative embodiments, which are less preferred but not excluded, the present invention further provides chiral compounds comprising a racemic mixture or an isolated enantiomer having one (an isolated enantiomer) or both (a racemic mixture) of the following formulae:

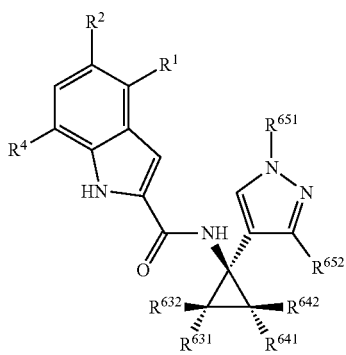

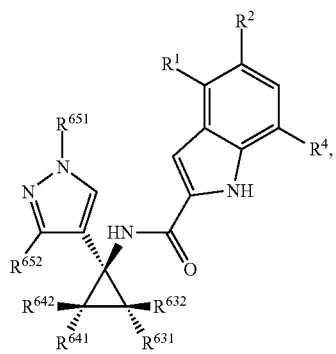

wherein R² is selected from —Cl, —Br and —CN; R¹ and R⁴ are independently selected from —H and —F; $R^{631}$, $R^{632}$, $R^{641}$ and $R^{642}$ are independently selected from —H, —F and substituted or unsubstituted $C_1$-$C_3$ alkyl groups; and $R^{651}$ and $R^{652}$ are independently selected from —H and substituted or unsubstituted $C_1$-$C_3$ alkyl groups and substituted or unsubstituted phenyl groups; and wherein $R^{642}$ is a sterically larger group than any of $R^{631}$, $R^{632}$ and $R^{641}$.

Thus, in some embodiments of the invention, the following chiral compounds having one (an isolated enantiomer) or both (a racemic mixture) of the following formulae are employed:

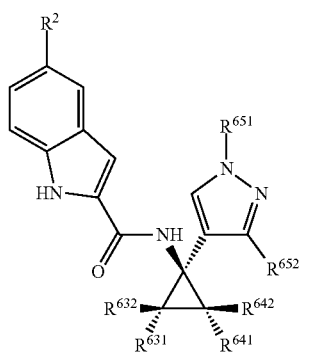

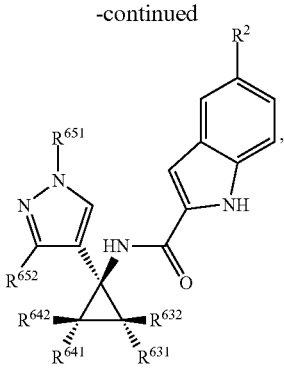

wherein R² is selected from —Cl, —Br and —CN; $R^{631}$, $R^{632}$, $R^{641}$ and $R^{642}$ are independently selected from —H, —F and substituted or unsubstituted $C_1$-$C_3$ alkyl groups; $R^{651}$ and $R^{652}$ are independently selected from —H and substituted or unsubstituted $C_1$-$C_3$ alkyl groups and substituted or unsubstituted phenyl groups; and wherein $R^{642}$ is a sterically larger group than any of $R^{631}$, $R^{632}$ and $R^{641}$.

In further embodiments of the invention, the following chiral compounds having one (an isolated enantiomer) or both (a racemic mixture) of the following formulae are employed:

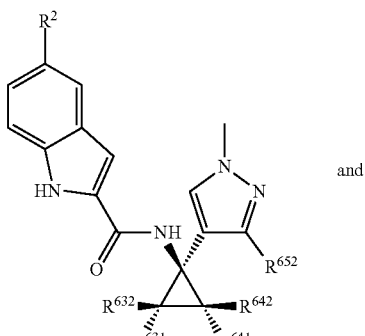

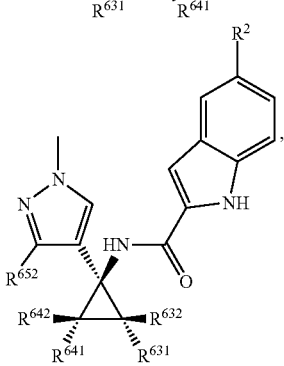

wherein R² is selected from —Cl, —Br and —CN; $R^{631}$, $R^{632}$, $R^{641}$ and $R^{642}$ are independently selected from —H, —F and substituted or unsubstituted $C_1$-$C_3$ alkyl groups; $R^{652}$ is selected from —H and substituted or unsubstituted $C_1$-$C_3$ alkyl groups and substituted or unsubstituted phenyl groups; and wherein $R^{6422}$ is a sterically larger group than any of $R^{631}$, $R^{632}$ and $R^{641}$.

In further embodiments of the invention, the following chiral compounds having one (an isolated enantiomer) or both (a racemic mixture) of the following formulae are employed:

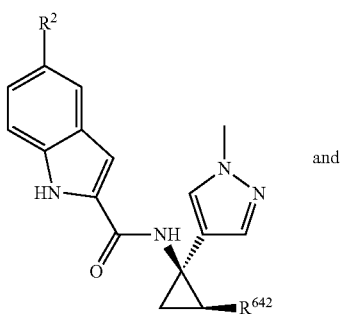

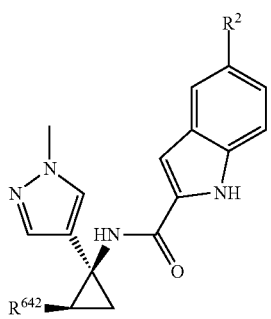

wherein R² is selected from —Cl, —Br and —CN; and wherein $R^{642}$ is independently selected from —F and substituted or unsubstituted $C_1$-$C_3$ alkyl groups.

Thus, in embodiments of the invention, isolated enantiomers and racemic mixtures of the following chiral compounds may be employed:

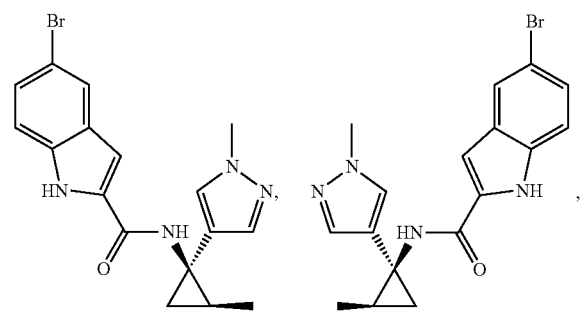

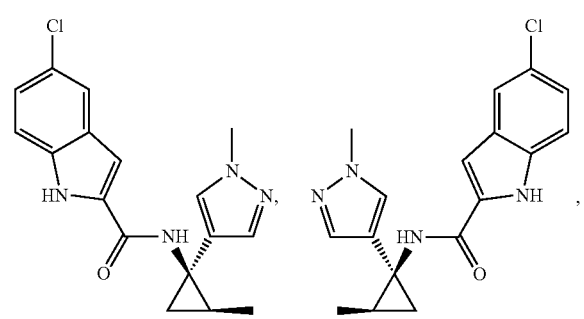

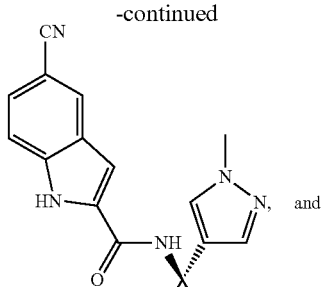

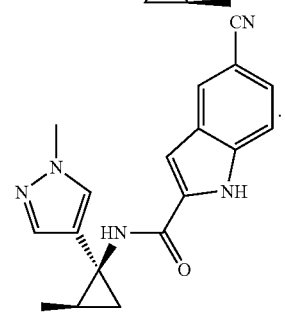

The nature of the R groups will now be described in more detail.

In typical embodiments, both of $R^1$ and $R^4$ are —H. However, in alternative embodiments $R^1$ is —F and $R^4$ is —H, or $R^1$ is —H and $R^4$ is —F, or $R^1$ is —F and $R^4$ is —F. It is most preferred that both of $R^1$ and $R^4$ are —H and preferred that one of $R^1$ and $R^4$ is —F and the other is —H, whilst is less typical embodiments both of $R^1$ and $R^4$ may be —F.

In typical embodiments at least one of $R^{631}$, $R^{632}$, $R^{641}$ and $R^{642}$ is not —H. In other embodiments two or more, three or more, or all of $R^{631}$, $R^{632}$, $R^{641}$ and $R^{642}$ are not —H. In such embodiments, it is preferred that one or both of $R^{641}$ and $R^{642}$ is not —H, and more preferably that $R^{642}$ is not —H. Thus in the most preferred embodiments, $R^{631}$, $R^{632}$ and $R^{641}$ are —H and $R^{642}$ is not —H. However, other embodiments in which all of $R^{631}$, $R^{632}$, $R^{641}$ and $R^{642}$ are —H are not excluded.

When one or more of $R^{631}$, $R^{632}$, $R^{641}$ and $R^{642}$ is a substituted or unsubstituted $C_1$-$C_3$ alkyl group, the $C_1$-$C_3$ alkyl group may typically be selected from methyl (Me), ethyl (Et), propyl (Pr) and iso-propyl (i-Pr) groups. When the $C_1$-$C_3$ alkyl group is a substituted $C_1$-$C_3$ alkyl group it may typically be selected from alkyl groups with fluorine substituents, such as —$CH_2F$, —$CHF_2$, and —$CF_3$.

In more preferred embodiments $R^{642}$ is preferably -Me, —$CF_3$, or —F. In such embodiments, it is particularly preferred that $R^{631}$, $R^{632}$ and $R^{641}$ are —H.

$R^{651}$ and $R^{652}$ may be the same or different since they are selected independently. In typical embodiments at least one of $R^{651}$ and $R^{652}$ is not —H. In yet other typical embodiments both of $R^{651}$ and $R^{652}$ are not —H. However, other embodiments in which both of $R^{651}$ and $R^{652}$ are —H are not excluded.

When one or both of $R^{651}$ and $R^{652}$ is a substituted or unsubstituted $C_1$-$C_3$ alkyl group, the $C_1$-$C_3$ alkyl group may typically be selected from methyl (Me), ethyl (Et), propyl (Pr) and iso-propyl (i-Pr) groups. When the $C_1$-$C_3$ alkyl group is a substituted $C_1$-$C_3$ alkyl group it may typically be selected from alkyl groups with fluorine substituents, such as —$CH_2F$, —$CHF_2$, and —$CF_3$.

When one or both of $R^{651}$ and $R^{652}$ is a substituted or unsubstituted phenyl group, typically the phenyl group is unsubstituted, i.e. is -Ph. If one of these groups is a phenyl group, it is more preferred that $R^{651}$ is phenyl rather than $R^{652}$.

In more embodiments, $R^{651}$ is -Me and $R^{652}$ is —H, -Et or -iPr.

Thus, the present invention provides isolated enantiomers, racemic mixtures and achiral compounds having the following formulae (the absolute stereochemistries are not yet known, but the (+) enantiomers are preferred and can be identified by standard means (such as by measuring their optical rotation), as demonstrated in the Examples herein):

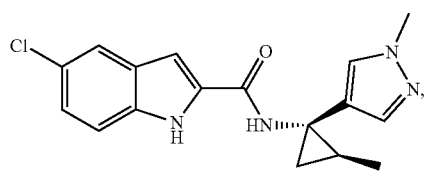

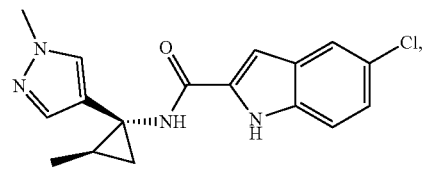

isolated (+) and (−) enantiomers and racemic mixture 1: [(+) 1, (−) 1 and rac 1],

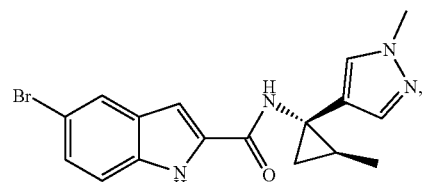

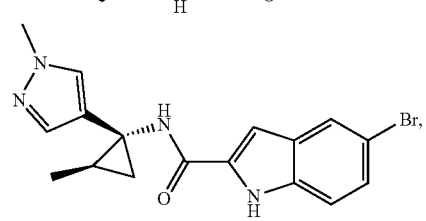

isolated (+) and (−) enantiomers and racemic mixture 2: [(+) 2, (−) 2 and rac 2],

3

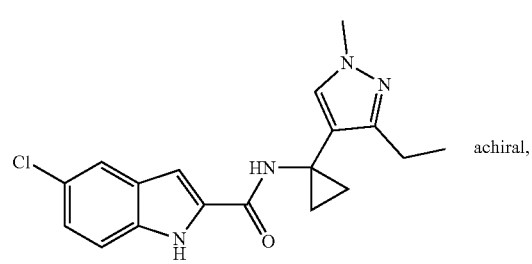

achiral,

-continued

4

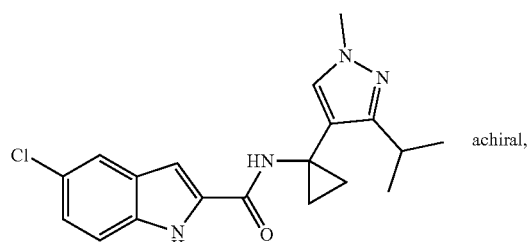

achiral,

5

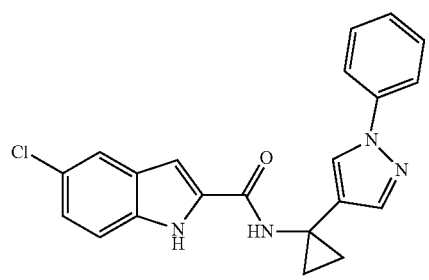

achiral,

6

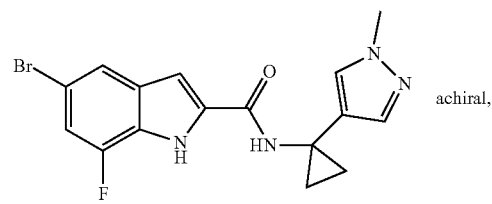

achiral,

7

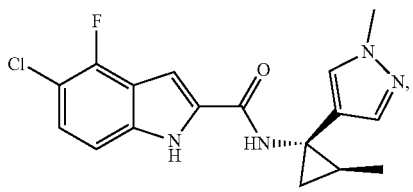

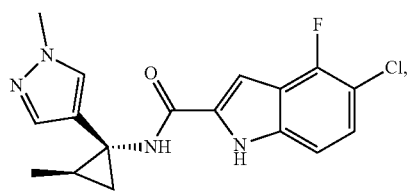

isolated (+) and (−) enantiomers and racemic mixture 7: [(+) 7, (−) 7 and rac 7],

8

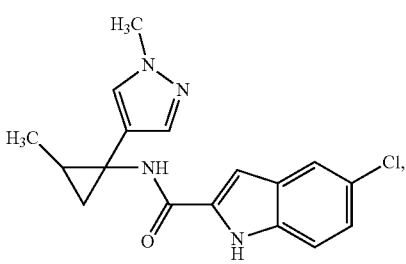

-continued

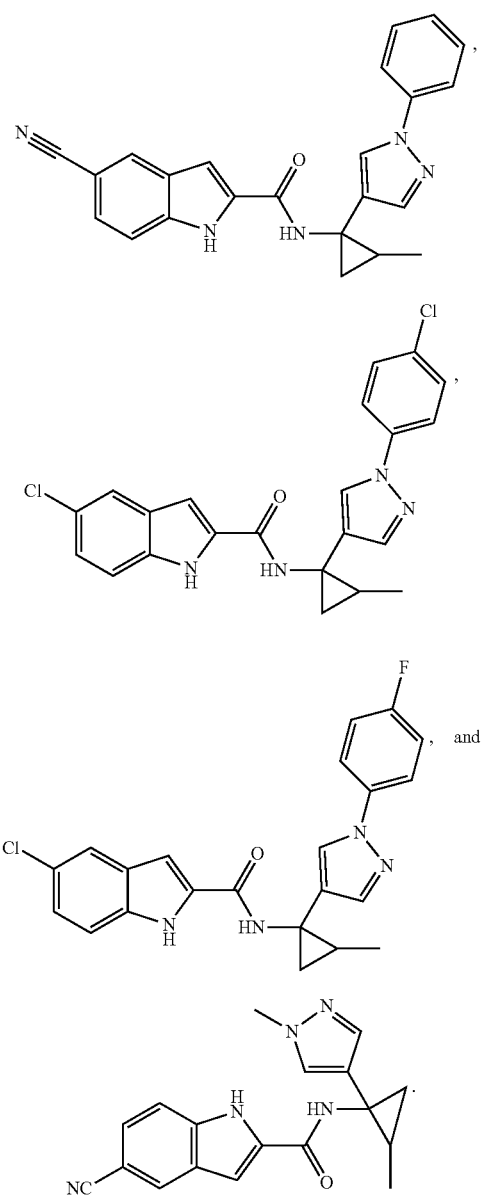

In some instances, the formulae herein are shown in non-stereoisomeric form, in other cases in stereoisomeric form. For the avoidance of doubt, where stereochemistry is not explicitly indicated, in the present context a single formula is intended to represent all possible stereoisomers of a particular structure, including all possible isolated enantiomers corresponding to the formula, all possible mixtures of enantiomers corresponding to the formula, all possible mixtures of diastereomers corresponding to the formula (e.g. where there is more than one chiral centre), all possible mixtures of epimers corresponding to the formula, all possible racemic mixtures corresponding to the formula, and all possible cis and trans isomers corresponding to the formula. In addition to this, the above formulae (and all formulae herein) are intended to represent all tautomeric forms equivalent to the corresponding formula.

In the context of the present invention, the medicinal use is not especially limited, provided that it is a use which is facilitated by the IDO inhibitory effect of the compound. Thus, the compounds of the invention may be for use in any disease, condition or disorder that may be prevented, ameliorated or treated using an IDO inhibitor. Typically this comprises a disease condition and/or a disorder selected from: a cancer, an inflammatory condition, an infectious disease, a central nervous system disease or disorder, coronary heart disease, chronic renal failure, post anaesthesia cognitive dysfunction, a disease condition and/or a disorder relating to female reproductive health including contraception or abortion, and cataracts.

When the disease, condition or disorder is an inflammatory disease, condition or disorder, it is not especially limited, provided that the disease, condition or disorder is one which may be treated, prevented or ameliorated by using an IDO inhibitor. However, typically the inflammatory condition is a condition relating to immune B cell, T cell, dendritic cell, natural killer cell, macrophage, and/or neutrophil dysregulation.

When the disease, condition or disorder is a cancer, it is not especially limited, provided that the cancer is one which may be treated, prevented or ameliorated by using an IDO inhibitor. Thus the cancer may be a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, esophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, Proteus syndrome, and Proteus-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelomonocytic leukaemia, Hodgkin lymphoma, non-Hodgkin lymphoma, mantle lymphoma, follicular lymphoma, primary effusion lymphoma. AIDS-related lymphoma, Hodgkin lymphoma, diffuse B cell lymphoma, Burkitt lymphoma, and cutaneous T-cell lymphoma). More typically (but not exclusively) the cancer is a cancer selected from acute myeloid leukemia (AML), a small-cell lung cancer, a melanoma, an ovarian cancer, a colorectal cancer, a pancreatic cancer, an endometrial cancer, and a skin papilloma.

When the disease is an infectious disease, it is not especially limited, provided that the disease is one which may be treated, prevented or ameliorated by using an IDO inhibitor. However, typically the infectious disease is selected from a bacterial infection and a viral infection, preferably a gut infection, sepsis, sepsis induced hypotension, HIV infection and HCV infection.

When the disease, condition or disorder is a central nervous system disease, condition or disorder, it is not especially limited, provided that the disease, condition or disorder is one which may be treated, prevented or ameliorated by using an IDO inhibitor. However, the central nervous system disease, condition or disorder is typically selected from amyotrophic lateral sclerosis (ALS), Huntington's disease, Alzheimer's disease, pain, a psychiatric disorder, multiple sclerosis, Parkinson's disease, and HIV related neurocognitive decline.

When the disease, condition or disorder is one relating to female reproductive health, it is not especially limited provided that the disease, condition or disorder is one which may be treated, prevented or ameliorated by using an IDO inhibitor. In typical embodiments the disease, condition or disorder is selected from gynaecological disorders such as endometriosis. Conditions relating to female reproductive health that are included in the invention include contraception and abortion such that the compounds of the invention may be used as a contraceptive and/or abortive agent.

The present invention also provides a pharmaceutical composition comprising a compound as defined above. Whilst the pharmaceutical composition is not especially limited, typically the composition further comprises a pharmaceutically acceptable additive and/or excipient. In the pharmaceutical composition, the compound as defined above may be present in the form described above, but may alternatively be in a form suitable for improving bioavailability, solubility, and/or activity, and/or may be in a form suitable for improving formulation. Thus, the compound may be in the form of a pharmaceutically acceptable salt, hydrate, acid, ester, or other alternative suitable form. Typically, the composition is for treating a disease, condition or disorder as defined above. In some instances, the compound may be present in the composition as a pharmaceutically acceptable salt, or other alternative form of the compound, in order to ameliorate pharmaceutical formulation.

In some embodiments the pharmaceutical composition is a composition for treating a cancer, further comprising a further agent for treating cancer. The further agent for treating cancer is not especially limited, provided that it affords some utility for cancer treatment. However, typically the further agent for treating cancer is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors. An immunotherapeutic agent may consist of but is not limited to an anti-tumour vaccine, an oncolytic virus, an immune stimulatory antibody such as anti-CTLA4, anti-PD1, anti-PDL-1, anti-OX40, anti-41BB, anti-CD27, anti-anti-CD40, anti-LAG3, anti-TIM3, and anti-GITR, a novel adjuvant, a peptide, a cytokine, a chimeric antigen receptor T cell therapy (CAR-T), a small molecule immune modulator, tumour microenvironment modulators, and anti-angiogenic agents.

Further provided by the invention is a method of treating a disease and/or a condition and/or a disorder, which method comprises administering to a patient a compound or a composition as defined above. The method is typically a method for treating any disease condition or disorder mentioned herein. In typical embodiments, the method is a method for treating a cancer. Preferably such a method comprises administering to a patient a compound or a composition as defined above and a further agent for treating cancer as defined above. The compound or composition and the further agent may administered simultaneously, sequentially or separately, depending upon the agents and patients involved, and the type of cancer indicated.

Typically, in all embodiments of the invention, both above and below, the patient is an animal, typically a mammal, and more typically a human.

Further provided by the invention is a method of synthesis of a compound as defined above, which method comprises performing a coupling reaction (such as an amide coupling reaction) on a substituent in the indole 2-position.

The invention will now be described in more detail, by way of example only, with reference to the following specific embodiments.

EXPERIMENTAL

The following examples are intended to be illustrative only and not limiting in any way. Abbreviations used are those conventional in the art or the following.
ACN acetonitrile
° C. degree Celsius
DCM dichloromethane
DMA dimethylamine
DMF N,N-dimethylformamide
DMSO dimethylsulfoxide
EtOAc ethyl acetate
EtOH ethanol
g gram
h hour(s)
HPLC high pressure liquid chromatography
kg kilogram
L liter
LC liquid chromatography
LCMS liquid chromatography and mass spectrometry
Me methyl
MeOH methanol
MS mass spectrometry
MTBE methyl tert-butyl ether
min minutes
mL milliliter(s)
m/z mass to charge ratio
nm nanometer
nM nanomolar
N normal
MR nuclear magnetic resonance
rt or RT room temperature
sat. saturated
TEA triethyl amine
FA trifluoroacetic acid
THF tetrahydrofuran Exemplary compounds of the invention were prepared, and tested to determine their effect as IDO inhibitors. These were compared with reference compounds REF 1, REF 2, and REF 3, which are disclosed in PCT publication WO2015150097:

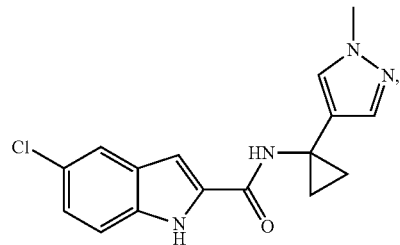

REF 1

-continued

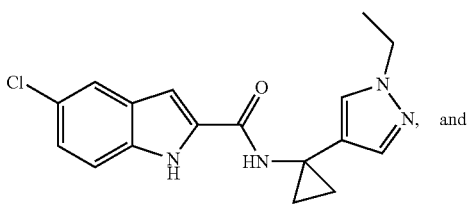

REF 2

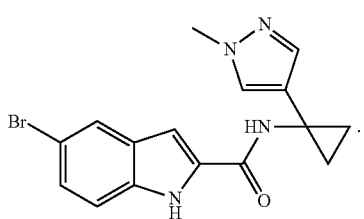

REF 3

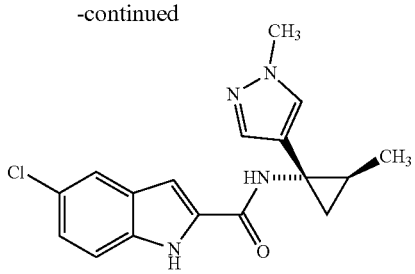

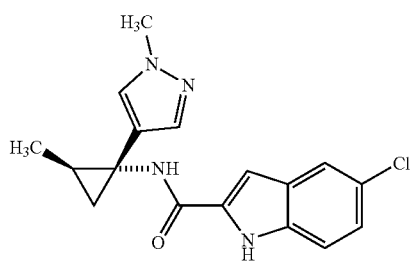

Compound 1
Enantiomers 1 and 2

EXAMPLES

As has been mentioned, the compounds disclosed herein may be synthesised using known coupling reactions, and starting materials that are readily available commercially. Exemplary syntheses of compounds 1 to 9 are shown below.

Example 1: Synthesis of Compound 1 (Racemic Mixture of Enantiomers (+) 1 and (−) 1)

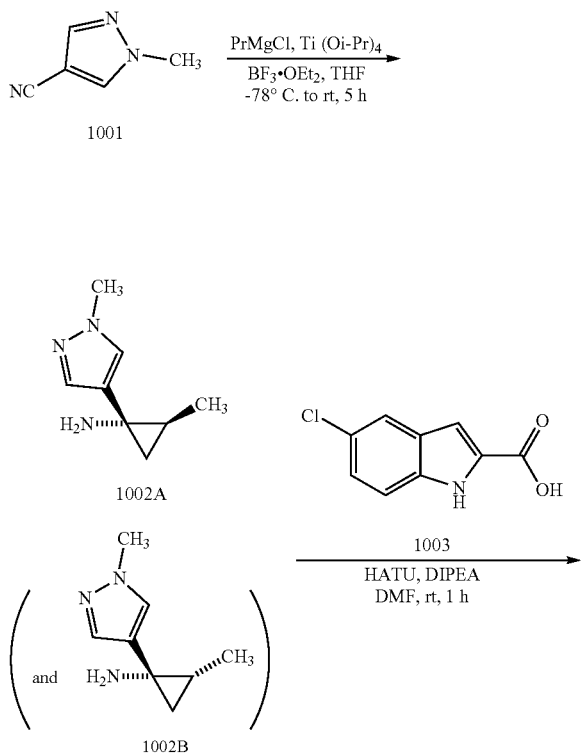

Preparation of Racemic 1002A and Racemic 1002B

To a solution of nitrile 1001 (25.0 g, 0.23 mol) in THF (135 mL) was added Ti(O-i-Pr)$_4$ (73 mL, 0.46 mol) at room temperature. To the above reaction mixture under argon atmosphere at −78° C. the Grignard reagent (500 mL, 0.58 mol) was added dropwise and the reaction mixture was stirred at −78° C. for 0.5 h. Then the reaction mixture was stirred at ambient temperature for 1 h. BF$_3$.OEt$_2$ (67.0 mL, 0.46 mol) was added to the above reaction mixture at room temperature and stirred for 1 h. After completion of the reaction, the reaction mixture was quenched with water (17 mL), HCl (2N, 30 mL) to adjust the pH to 3 and stirred for 15 min and then basified with 6N NaOH (adjust the pH to 10). The organic layer was separated and the aqueous layer was extracted with 10% CH$_2$Cl$_2$/CH$_3$OH (200 mL×2). The combined organic layers were dried over anhydrous Na$_2$SO$_4$ and concentrated under reduced pressure. The crude residue was further purified by Combiflash column chromatography (CH$_2$Cl$_2$/CH$_3$OH, 0 to 10%) to separate racemic 1002A (4.0 g, 11%) (trans) and racemic 1002B (6.0 g, 14%) (cis) as reddish brown oils. MS (MM) m/z 152.1 [M+H]+.

$^1$H NMR of 2A (300 MHz, DMSO-d$_6$): δ 7.61 (s, 1H), 7.38 (s, 1H), 4.32 (bs, 3H), 4.02 (s, 3H), 1.25-1.21 (m, 1H), 1.20-1.16 (m, 1H), 1.00 (d, 2H), 0.78 (t, 1H).

Preparation of Compound 1 (Racemic Mixture of Enantiomers (+) 1 and (−) 1)

To a solution of 1003 (9.0 g, 0.046 mol) in DMF was added racemic 1002A (7.0 g, 0.046 mol) followed by HATU (26.0 g, 0.06 mol) and DIPEA (16.0 mL, 0.092 mol). The resulting reaction mixture was stirred at room temperature for 1 h. The reaction mixture was diluted with water (200 mL) and filtered, the obtained solid was further purified by Combiflash column chromatography (hexane/EtOAc, 1:1) to afford Compound 1 racemic mixture (2.42 g, 16%) as a solid. MS (MM) m/z 329.1 [M+H]+; HPLC: 96.9%, Zorbax-SB-CN, 220 nm $^1$H NMR (300 MHz, DMSO-d$_6$): δ 11.66 (s, 1H), 9.11 (s, 1H), 7.65 (d, 1H), 7.56 (s, 1H), 7.41 (d, 1H), 7.32 (s, 1H), 7.15 (dd, 1H), 7.07 (d, 1H) 3.76 (s, 3H), 1.32 (m, 1H), 1.26 (m, 1H), 0.89 (m, 4H).

Chiral Separation of Compound 1 into Enantiomers (+) 1 and (−) 1

Example 2: Synthesis of Compound 2 (Racemic Mixture of Enantiomers (+) 2 and (−) 2)

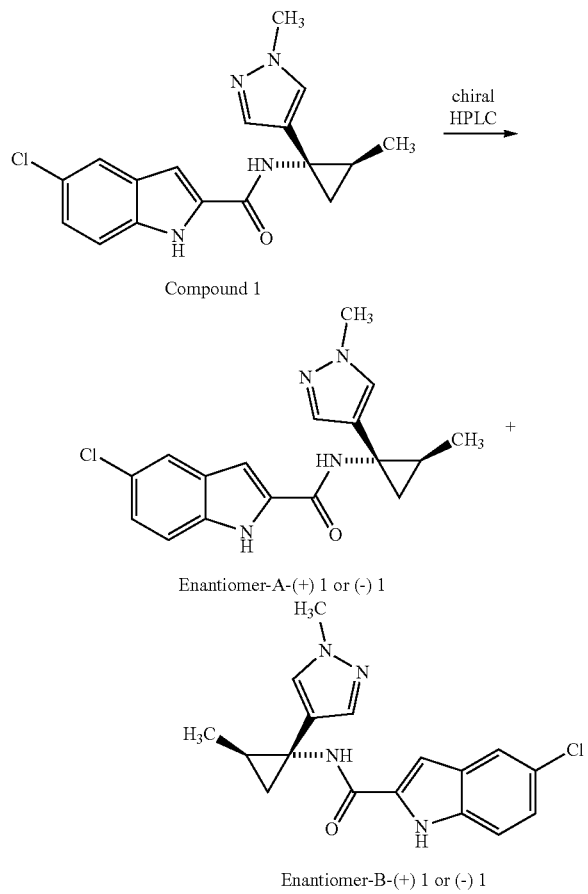

Compound 1

Enantiomer-A-(+) 1 or (−) 1

Enantiomer-B-(+) 1 or (−) 1

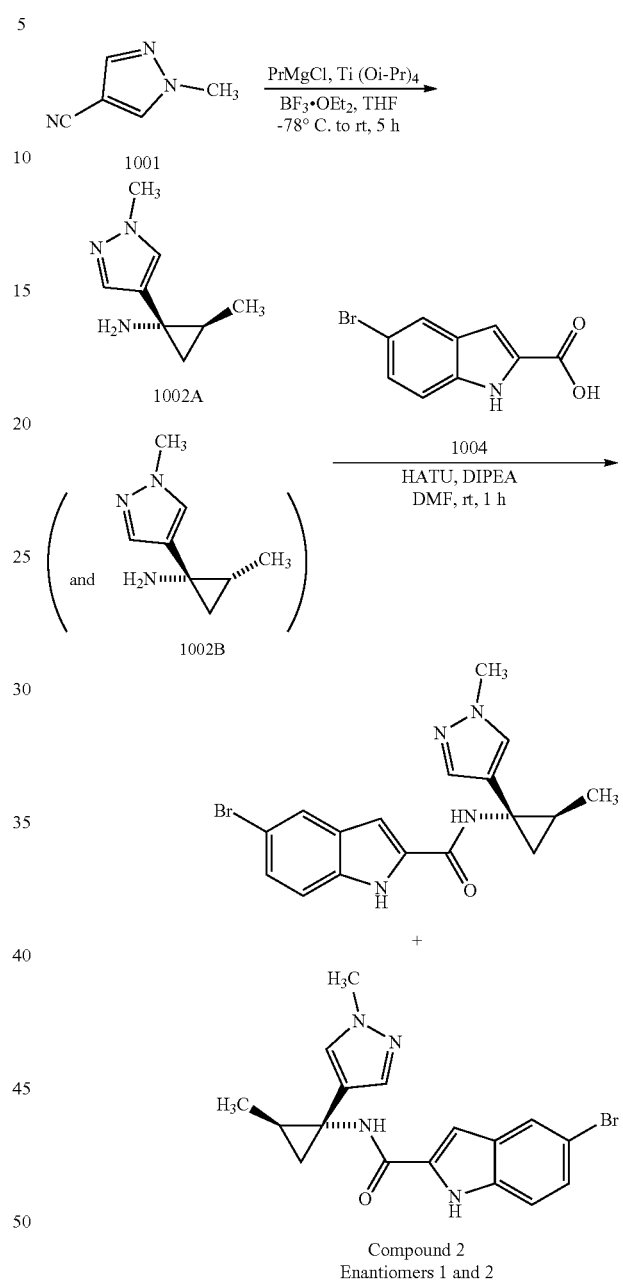

Compound 2
Enantiomers 1 and 2

Compound 1 (110 mg) was subjected to chiral chromatography to separate the enantiomers. Isolated compound enantiomer (−) 1 (30.0 mg, 54%) was produced as an off-white solid and isolated compound enantiomer (+) 1 (21.9 mg) was also produced as an off-white solid.

HPLC Conditions Used for Purification

Column: Chiralcel OD-H 250×20 mm, 5 um (LOT #00H0CJ-QH004; Part #14245). Mobile phase:hexane:IPA (75:25% v/v); UV: 220 nm.

Analytical Data for (−) 1

MS (MM) m/z 329.1 [M+H]+; HPLC: >99%, Zorbax-SB-CN, 220 nm;

(−) 1: $[\alpha]^{25}_D$ −125.7° (c 0.1, methanol);

$^1$H NMR (300 MHz, DMSO-d$_6$): δ 11.66 (s, 1H), 9.11 (s, 1H), 7.65 (d, 1H), 7.56 (s, 1H), 7.41 (d, 1H), 7.32 (s, 1H), 7.15 (dd, 1H), 7.07 (d, 1H) 3.76 (s, 3H), 1.32 (m, 1H), 1.26 (m, 1H), 0.89 (m, 4H).

Analytical Data for (+) 1

MS (MM) m/z 329.1 [M+H]+; HPLC: >99%, Zorbax-SB-CN, 220 nm;

(+) 1: $[\alpha]^{25}_D$+119.2° (c 0.1, methanol);

$^1$H NMR (300 MHz, DMSO-d$_6$): δ 11.66 (s, 1H), 9.11 (s, 1H), 7.65 (d, 1H), 7.56 (s, 1H), 7.41 (d, 1H), 7.32 (s, 1H), 7.15 (dd, 1H), 7.07 (d, 1H) 3.76 (s, 3H), 1.32 (m, 1H), 1.26 (m, 1H), 0.89 (m, 4H).

Preparation of Compound 2 (Racemic Mixture of Enantiomers (+) 2 and (−) 2)

To a solution of 1004 (9.0 g, 0.037 mol) in DMF was added a crude mixture of racemic 1002A and racemic 1002B (19.0 g, as obtained from conversion of compound 1001 to 1002A/1002B as described above, but without separating the trans and cis isomers) followed by HATU (21.0 g, 0.056 mol) and DIPEA (13.0 mL, 0.075 mol) at room temperature. The resulting reaction mixture was stirred at room temperature for 1 h. After completion of the reaction, the reaction mixture was poured onto water (200 mL), filtered and the obtained solid was then further purified to separate the trans and cis isomers by Combiflash column chromatography using 120 g Redisep®, column (hexane/EtOAc, 1:1) to afford Compound 2 racemic mixture (2.40 g, 14%) as a solid. MS (MM) m/z 373.1 [M+H]+; HPLC: 96.9%, Zorbax-SB-CN, 220 nm.

¹H NMR (300 MHz, DMSO-d₆): δ 11.68 (s, 1H), 9.13 (s, 1H), 7.80 (s, 1H), 7.56 (s, 1H), 7.35 (t, 2H), 7.25 (d, 1H), 7.07 (s, 1H), 3.76 (s, 3H), 1.32 (m, 1H), 1.26 (m, 1H), 0.89 (m, 4H).

Chiral Separation of Compound 2 into Enantiomers (+) 2 and (−) 2

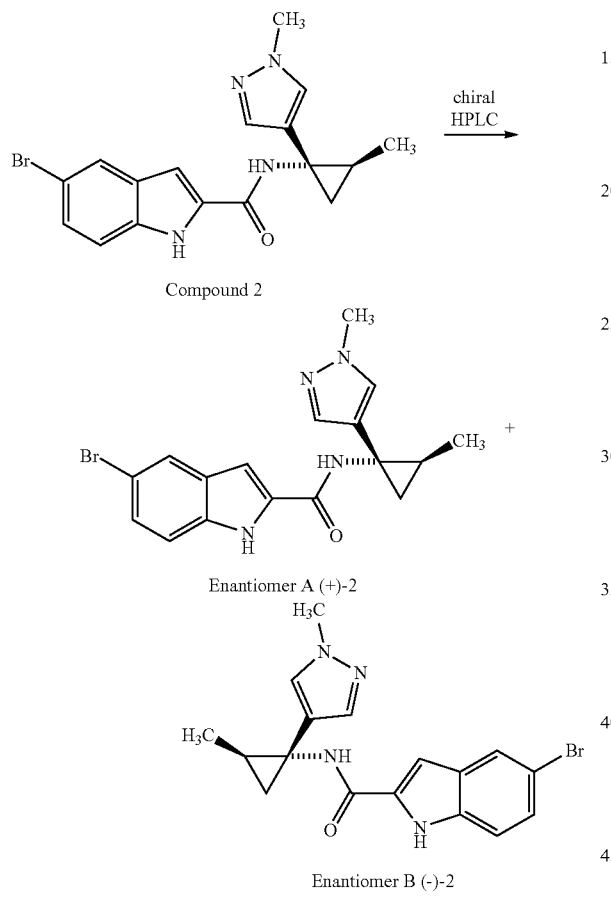

Compound 2 (110 mg) was subjected to chiral HPLC purification to separate the enantiomers. Isolated Compound 2 enantiomer (−) 2 (20 mg, rt, 9.64) and enantiomer (+) 2 (20 mg, rt, 13.59) were produced as a solids.

Prep HPLC Conditions Used for Purification

Column: Chiralcel OD-H 250×20 mm, 5 um (LOT #00H0CJ-QH004; Part #14245). Mobile phase:Hexane:IPA (75:25% v/v).

UV: 220 nm

Analytical Data for (−) 2

MS (MM) m/z 373.1 [M+H]+; HPLC: >99%, Zorbax-SB-CN, 220 nm;

(−) 2: [α]$^{25}_D$ −1200 (c 0.1, methanol):

¹H NMR (300 MHz, DMSO-d₆): δ 11.68 (s, 1H), 9.12 (s, 1H), 7.80 (dd, 1H), 7.56 (s, 1H), 7.35 (t, 2H), 7.25 (dd, 1H), 7.07 (dd, 1H), 3.76 (s, 3H), 1.32 (m, 1H), 1.26 (m, 1H), 0.89 (m, 4H).

Analytical Data for (+) 2

MS (MM) m/z 373.1 [M+H]+; HPLC: 99.0%, Zorbax-SB-CN, 220 nm;

(+) 2: [α]$^{25}_D$+110° (c 0.1, methanol);

¹H NMR (300 MHz, DMSO-d₆): δ 11.68 (s, 1H), 9.12 (s, 1H), 7.80 (dd, 1H), 7.56 (s, 1H), 7.35 (t, 2H), 7.25 (dd, 1H), 7.07 (dd, 1H), 3.76 (s, 3H), 1.32 (m, 1H), 1.26 (m, 1H), 0.89 (m, 4H).

Example 3: Synthesis of Compound 7 (Racemic Mixture of Enantiomers (+) 7 and (−) 7)

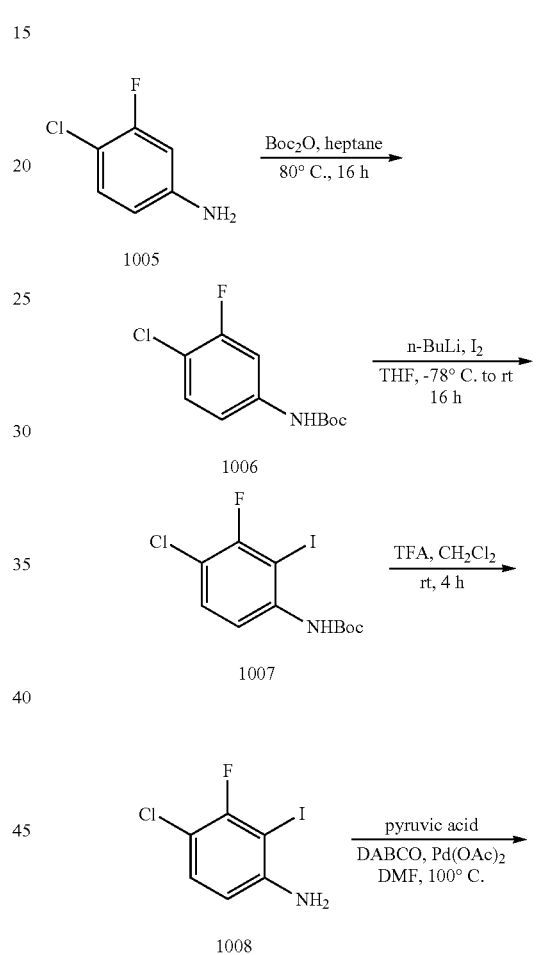

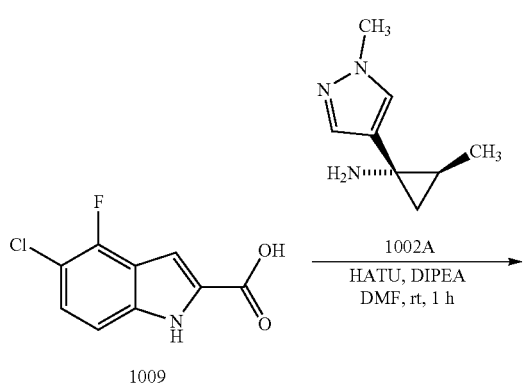

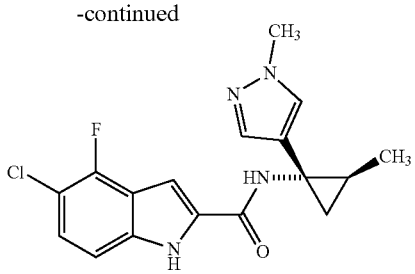

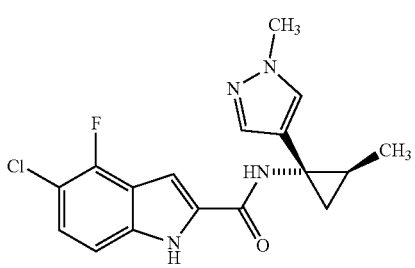

Compound 7
Enantiomers (+) 7 and (−) 7

Preparation of 1006

To a solution of 1005 (10.0 g, 68.7 mmol) in heptane (100 ml) was added (Boc)$_2$O (16.4 mL, 76.6 mmol). After stirring the reaction mixture at 80° C. for 16 h, solvent was evaporated and the residue was purified by Combiflash column chromatography (hexane/EtOAc, 1:2) to afford 1006 (7.0 g, 43%) as a solid. $^1$H NMR (400 MHz, CDCl$_3$): δ 7.44 (dd, 1H), 7.27 (t, 1H), 6.94 (dd, 1H), 6.53 (s, 1H), 1.50 (s, 9H).

Preparation of 1007

To a solution of 1006 (7.0 g, 28.5 mmol) in THF (70 mL) was added n-BuLi (2.5M) (34.2 mL, 85.5 mmol) at −78° C. After stirring the reaction mixture for 0.5 h, iodine (25.2 g 99.7 mmol) in THF was added at −78° C. Then the reaction mixture was stirred at −78° C. for 2 h and quenched with aq. NH$_4$Cl (50 mL) and extracted with EtOAc (2×100 mL). The combined organic layers were dried over anhydrous Na$_2$SO$_4$ and purified by Combiflash column chromatography (hexane/EtOAc, 1:2) to afford 1007 (5.0 g, crude) as a solid.

Preparation of 1008

To a solution of 1007 (3.0 g, 8.0 mmol) in CH$_2$Cl$_2$ (30 mL) was added TFA (10.0 mL) at room temperature. After stirring the reaction mixture at room temperature for 16 h, solvent was evaporated and the crude was washed with hexane (20 mL) to afford 1008 (1.0 g, crude) as a solid.

Preparation of 1009

To a solution of 1008 (3.0 g, 11.07 mmol) in DMF (40 ml) was added pyruvic acid (2.4 mL, 33.2 mmol) and DABCO (3.7 mL, 33.2 mmol). Then the reaction mixture was degassed with argon for 10 min and Pd(OAc)$_2$ (246 mg) was added. After stirring the reaction mixture at 100° C. for 3 h, water (15 ml) was added to the reaction mixture and then extracted with EtOAc (2×30 mL). The combined organic layers were dried over anhydrous Na$_2$SO$_4$ and concentrated under reduced pressure. The crude residue was purified by Combiflash column chromatography (hexane/EtOAc, 1:2) to afford 1009 (1.0 g, 43%) as a solid. $^1$H NMR (300 MHz, DMSO-d$_6$): δ 12.32 (s, 1H), 7.31 (q, 2H), 7.12 (s, 1H).

Preparation of Compound 7 (Racemic Mixture of Enantiomers (+) 7 and (−) 7)

To a solution of 1009 (100 mg, 4.69 mmol) in DMF was added 1002A (as obtained from conversion of compound 1001 to 1002A/1002B as described above) (71 mg, 4.69 mmol) followed by HATU (267 mg, 7.03 mmol) and DIPEA (0.16 mL, 9.38 mmol). After being stirred at room temperature for 1 h, the reaction mixture was diluted with water (20 mL) and then the solid was collected by filtration and further purified by Combiflash column chromatography (hexane/EtOAc, 1:1) to afford Compound 7 racemic mixture (42 mg, 26%) as a solid. MS (MM) m/z 347.1 [M+H]+; HPLC: 96.9%, Zorbax-SB-CN, 220 nm.

$^1$H NMR (300 MHz, DMSO-d$_6$): δ 12.0 (s, 1H), 9.18 (s, 1H), 7.56 (s, 1H), 7.33 (s, 1H), 7.24 (t, 3H), 3.76 (s, 3H), 1.32 (m, 1H), 1.18 (m, 1H), 0.91 (m, 4H).

Example 4: Synthesis of Compound 5

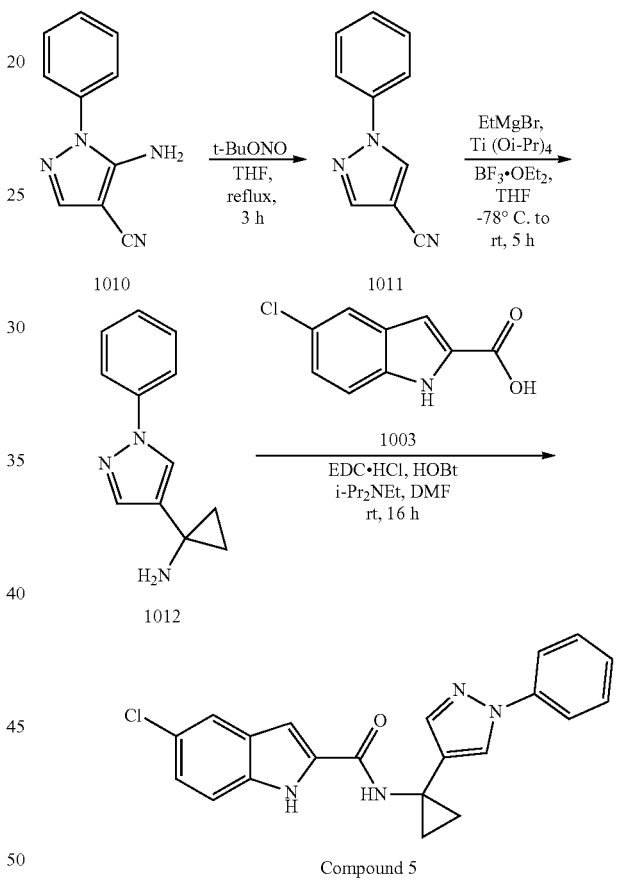

Compound 5

Preparation of 1011

To a solution of 1010 (1.0 g, 5.43 mmol) in THF (12 mL) was added t-BuONO (0.67 g, 6.52 mmol). After being stirred at reflux for 3 h, the reaction mixture was diluted with water (20 mL) and extracted with EtOAc (25 mL×3). Combined organic layers were dried over anhydrous Na$_2$SO$_4$ and concentrated under reduced pressure. Crude residue was purified by Combiflash column chromatography (hexanes EtOAc, 1:1) to afford 1011 (800 mg, 87%) as a solid. $^1$H NMR (300 MHz, CDCl$_3$): δ 8.31 (d, 1H), 8.00 (s, 1H), 7.68 (m, 2H), 7.52 (m, 2H), 7.43 (m, 1H).

Preparation of 1012

To a solution of nitrile 1011 (300 mg, 1.77 mmol) in THF (3 mL) was added Ti(O-i-Pr)$_4$ (0.6 mL, 1.94 mmol) at room temperature. Grignard reagent (4.5 mL, 4.43 mmol) was added to the reaction mixture dropwise under argon atmosphere at −78° C. and the reaction mixture was stirred at −78° C. for 0.5 h and then at ambient temperature for 1 h. To the above reaction mixture at room temperature BF$_3$.OEt$_2$ (0.5 mL, 3.54 mmol) was added and stirred for 1 h. After completion of reaction, the reaction mixture was quenched with water (3.0 mL), 2M HCl (2.0 mL) up to pH=3 and stirred for 15 min and then basified with 6N NaOH up to pH=10. The reaction mixture was extracted with 10% CH$_2$Cl$_2$/MeOH (15 mL×3). The combined organic layers were dried over anhydrous Na$_2$SO$_4$ and concentrated under reduced pressure. The crude residue was further purified by Combiflash column chromatography (CH$_2$Cl$_2$/MeOH, 0 to 10%) to afford 1012 (60 mg, 17%) as an oil. MS (MM) m/z 199.1 [M+H]+.

Preparation of Compound 5

To a solution of 1012 (60 mg, 0.30 mmol) in DMF (1.2 mL) was added 1003 (58 mg, 0.30 mmol) followed by EDC.HCl (115 mg, 0.60 mmol), HOBT (81 mg, 0.60 mmol) and DIPEA (0.15 mL, 0.60 mol). After stirring the reaction mixture at room temperature for 16 h. the reaction mixture was diluted with water (15 mL), the solid was collected by filtration and further purified by Combiflash column chromatography (hexane/EtOAc, 1:1) to afford 5 (10 mg, 11%) as a solid. MS (MM) m/z 377.0[M+H]+; HPLC: >99%, Eclipse XDB C18, 220 nm $^1$H NMR (400 MHz, DMSO-d$_6$): δ 11.73 (s, 1H), 9.22 (s, 1H), 8.26 (s, 1H), 7.77 (d, 2H), 7.69 (s, 1H), 7.58 (s, 1H), 7.44 (m, 3H), 7.26 (t, 1H), 7.18 (t, 2H), 1.22 (d, 4H).

Example 5: Synthesis of Compound 4 temperature. To the above reaction mixture under argon atmosphere at −15° C. the Grignard reagent (2.7 mL, 8.3 mmol) was added dropwise and the reaction mixture was stirred at −15° C. for 0.5 h and then the solution was stirred at ambient temperature for 1 h. BF$_3$.OEt$_2$ (1.4 mL, 9.9 mmol) was added to the above reaction mixture at room temperature and stirred for 1 h. After completion of reaction, the reaction mixture was quenched with water (1 mL), 2M HCl (3 mL) up to pH=3 and stirred for 15 min and then basified with 6N NaOH up to pH=10. The organic layer was collected and the aqueous layer was extracted with EtOAc (20 mL×2). The combined organic layers were dried over anhydrous Na$_2$SO$_4$ and concentrated under reduced pressure to afford 1014 (500 mg) which was used in the next step without purification.

Preparation of Compound 4

To a solution of 1003 (200 mg, 1.0 mmol) in DMF (10 mL) was added 1014 (196 mg, 1.1 mmol) followed by HATU (760 mg, 2.0 mmol), and DIPEA (0.5 mL, 3.0 mmol). The resulting reaction mixture was stirred at room temperature for 1 h. The reaction mixture was diluted with water (20 mL) and filtered and the obtained solid was further purified by Combiflash column chromatography (hexanes/EtOAc, 1:1) to afford Compound 4 (95 mg, 24%) as a solid. MS (MM) m/z 357.9 [M+H]+; HPLC: 98%, Eclipse XDB C18, 220 nm.

$^1$H NMR (300 MHz, DMSO-d$_6$): δ 11.66 (s, 1H), 8.91 (s, 1H), 7.65 (s, 1H), 7.45 (s, 1H), 7.34 (d, 1H), 7.15 (m, 2H), 3.69 (s, 3H), 2.56 (m, 1H), 1.19 (d, 6H), 1.19 (m, 4H).

Example 6: Synthesis of Compound 3

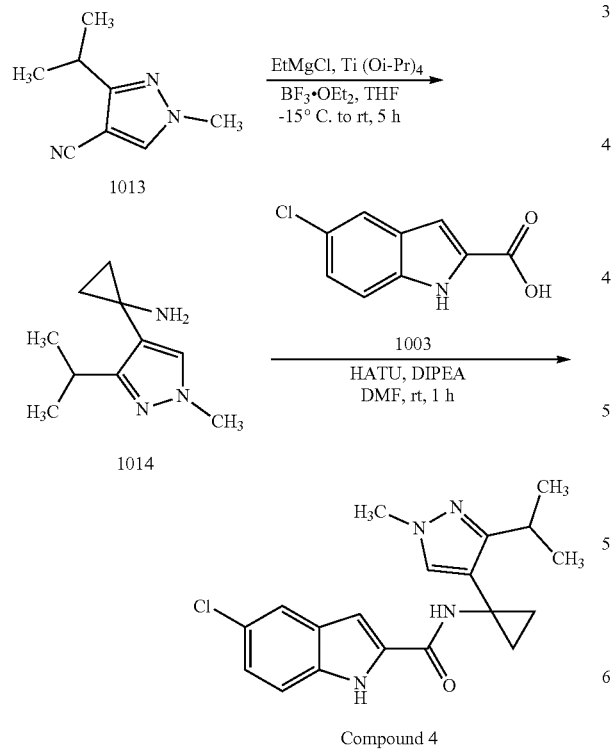

Compound 4

Preparation of 1014

To a solution of nitrile 1013 (500 mg, 3.3 mmol) in THF (10 mL) was added Ti(O-i-Pr)$_4$ (1 mL, 8.3 mmol) at room

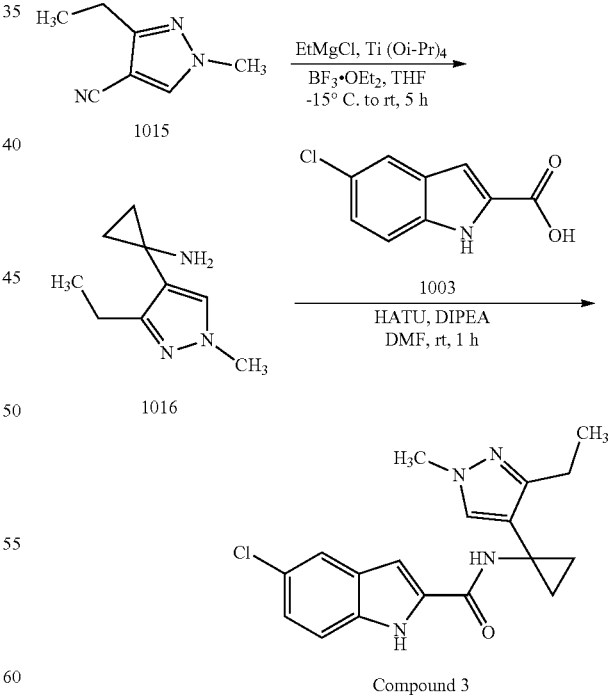

Compound 3

Preparation of 1016

To a solution of nitrile 1015 (500 mg, 3.7 mmol) in THF (10 mL) was added Ti(O-i-Pr)$_4$ (1.1 mL, 4.0 mmol) at room temperature. To the above reaction mixture under argon atmosphere at −15° C. the Grignard reagent (3.0 mL, 9.2 mmol) was added dropwise and the reaction mixture was stirred at −15° C. for 0.5 h and then the solution was stirred at ambient temperature for 1 h. BF$_3$.OEt$_2$ (1.0 mL, 7.4 mmol) was added to the above reaction mixture at room temperature and stirred for 1 h. After completion of the reaction, the reaction mixture was quenched with water (1 mL), 2M HCl (3 mL) up to pH=3 and stirred for 15 min and then basified with 6N NaOH up to pH=10. The organic layer was collected and the aqueous layer was extracted with EtOAc (20 mL×2). The combined organic layers were dried over anhydrous Na$_2$SO$_4$ and concentrated under reduced pressure to afford 1016 (300 mg) which was used in the next step without purification.

Preparation of Compound 3

To a solution of 1003 (200 mg, 1.0 mmol) in DMF (10 mL) was added 1016 (186 mg, 1.1 mmol) followed by HATU (760 mg, 2.0 mmol) and DIPEA (0.5 mL, 3 mmol). The resulting reaction mixture was stirred at room temperature for 1 h. The reaction mixture was diluted with water (20 mL), filtered and the obtained solid was further purified by Combiflash column chromatography (hexane/EtOAc, 1:1) to afford Compound 3 (55 mg, 13%) as a solid. MS (MM) m/z 342.8 [M+H]+; HPLC: 99%, Eclipse XDB C18, 220 nm.

$^1$H NMR (300 MHz, DMSO-d$_6$): δ 11.66 (s, 1H), 8.99 (s, 1H), 7.67 (s, 1H), 7.56 (s, 1H), 7.35 (d, 1H), 7.16 (d, 1H), 7.09 (s, 1H), 3.67 (s, 3H), 2.69 (q, 2H), 1.15 (m, 5H), 0.96 (m, 2H).

Example 7: Synthesis of Compound 6

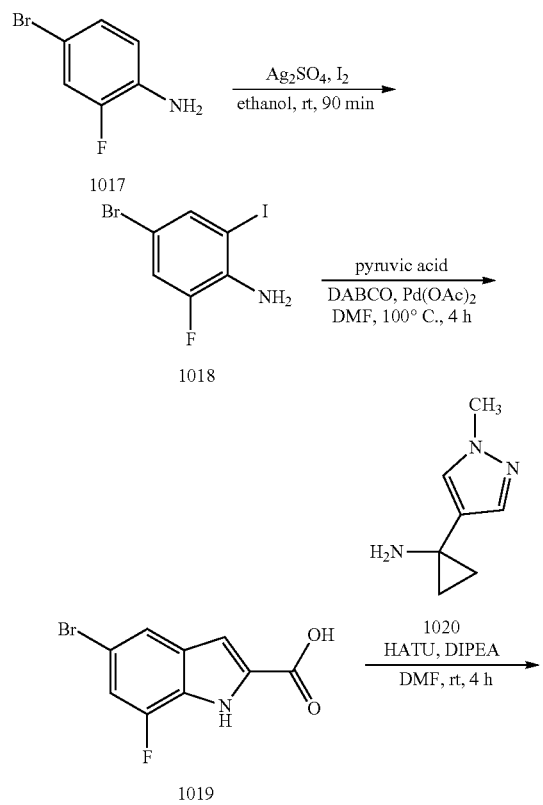

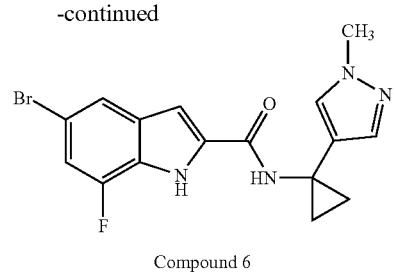

Compound 6

Preparation of 1018

To a solution of 1017 (10.0 g, 52.6 mmol) in ethanol (50 ml) was added silver sulphate (16.4 g, 52.6 mmol) and I$_2$ (25.2 g, 99.9 mmol). The resulting reaction mixture was stirred at room temperature for 3 h. Solvent was evaporated from the reaction mixture, the crude compound was washed with sodium thiosulfate solution (3×20 ml) then extracted with EtOAC (3×50 mL). The combined organic layers were dried over anhydrous Na$_2$SO$_4$ and concentrated under reduced pressure. The crude residue was purified by Combiflash column chromatography (hexane/EtOAc, 1:2) to afford 1018 (13 g, 79%) as a solid. $^1$H NMR (300 MHz, CDCl$_3$): δ 7.54 (s, 1H), 7.15 (dd, 1H), 4.12 (s, 1H).

Preparation of 1019

To a solution of 1018 (13.0 g, 41.2 mmol) in DMF (50 ml) was added pyruvic acid (10.89 mL, 123.8 mmol) and DABCO (13.8 mL, 123.8 mmol). The reaction mixture was degassed with argon for 10 min and Pd(OAc)$_2$ (923 mg, 4.12 mmol) was added at room temperature. After stirring the reaction mixture at 100° C. for 3 h, water (50 ml) was added to the reaction mixture which was then extracted with EtOAc (2×50 mL). The combined organic layers were dried over anhydrous Na$_2$SO$_4$ and concentrated under reduced pressure. The crude residue was purified by Combiflash column chromatography (hexane/EtOAc, 1:2) to afford 1019 (2.0 g, 19%) as a solid. $^1$H NMR (300 MHz, DMSO-d$_6$): δ 13.25 (bs, 1H), 12.52 (s, 1H), 7.71 (s, 1H), 7.33 (d, 1H), 7.15 (s, 1H).

Preparation of Compound 6

To a solution of 1019 (200 mg, 0.77 mmol) in DMF (10 mL) was added 1020 (116 mg, 0.85 mmol) followed by HATU (585 mg, 1.54 mmol) and DIPEA (0.4 mL, 2.31 mmol). The resulting reaction mixture was stirred at room temperature for 1 h. The reaction mixture was diluted with water (20 mL), filtered and the solid obtained was further purified by Combiflash column chromatography (hexane/EtOAc, 1:1) to afford Compound 6 (65 mg, 22%) as a solid. MS (MM) m/z 377.1 [M+H]+; HPLC: 90.5%. Eclipse XDB C18, 220 nm.

$^1$H NMR (300 MHz, DMSO-d$_6$): δ 12.26 (s, 1H), 9.17 (s, 1H), 7.70 (s, 1H), 7.49 (s, 1H), 7.25 (m, 3H), 3.73 (s, 3H), 1.16 (m, 4H).

Example 8: Synthesis of Compound 8—Enantiomers 1 and 2

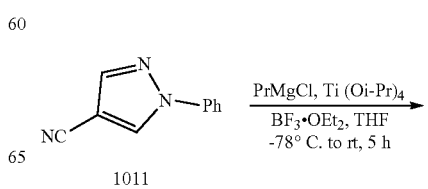

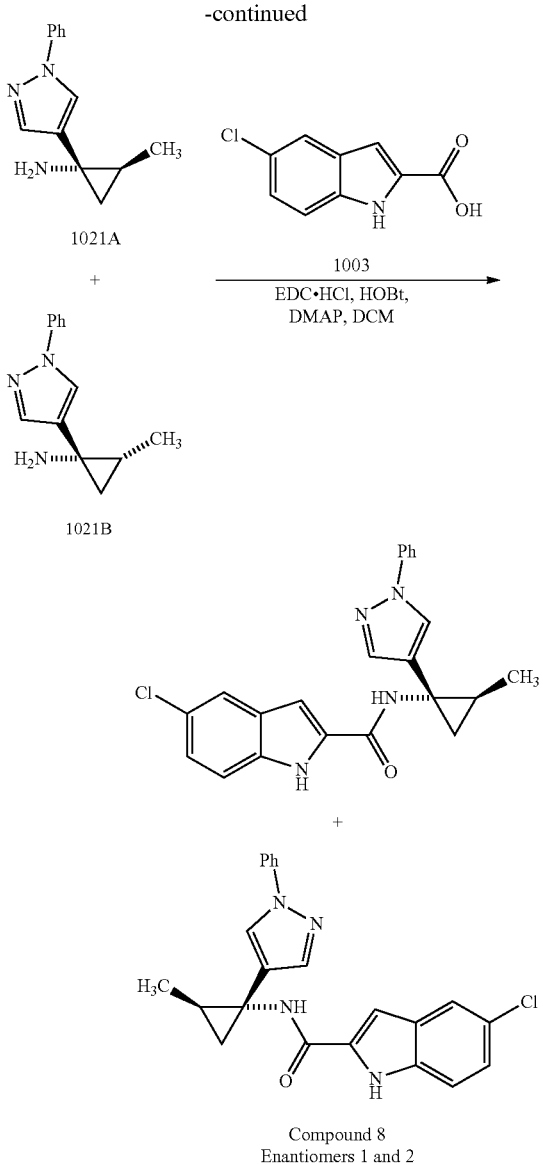

Preparation of Racemic 1021A and Racemic 1021

To a solution of nitrile 1011 (6.0 g, 35.5 mol) in THF (70 mL) at C was added Ti(O-i-Pr)₄ (1.09 mL, 39.05 mmol). To the above reaction mixture under argon atmosphere the 1M solution of Grignard reagent in THF (78.1 mL, 78.1 mmol) was added dropwise and the reaction mixture was stirred at −78° C. for 0.5 h. Then the reaction mixture was stirred at 0° C. for 1.5 h. BF₃.OEt₂ (10.0 mL, 71.1 mmol) was added to the above reaction mixture which was stirred for 0.5 h. After completion of the reaction, the reaction mixture was treated with HCl (2N, 30 mL) and stirred for 15 min and then basified with 6N NaOH. The mixture was extracted with ethyl acetate (3×100 mL) and the organic layers dried over anhydrous Na₂SO₄ and concentrated under reduced pressure. The crude residue was further purified by Combiflash column chromatography (ethyl acetate/hexane, 0 to 100%) to separate racemic 1021A (1.0 g) (trans) and racemic 1021B (0.8 g) (cis) oils.

MS (MM) m/z: 214.1 [M+H]⁺.

Preparation of Compound 8 Enantiomers 1 and 2

To a solution of 1003 (0.546 g, 2.8 mmol) in DCM (20 mL) was added racemic 1101A (0.5 g, 2.8 mmol) followed by ethylcarbodiimide hydrochloride (1.07 g, 5.6 mmol), hydroxybenzotriazole (0.756 g, 0.056 mol) and 4-dimethylaminopyridine (0.34 g, 2.8 mmol). The resulting reaction mixture was stirred at room temperature for 18 h. After completion of the reaction, the reaction mixture was poured onto water (30 mL) which was extracted with ethyl acetate (3×20 mL). The combined organic layers were dried over anhydrous sodium sulphate and evaporated. Purification by Combiflash column chromatography using a 40 g Redisep® column (EtOAc/hexane, 0-70%) afforded racemic Compound 8 as a solid.

Racemic Compound 8 (400 mg) was subjected to chiral HPLC purification to separate the enantiomers. Isolated Compound 8 enantiomer 1 (142 mg, rt, 20.39) and enantiomer 2 (129 mg, rt, 25.81) were produced as solids.

Prep HPLC Conditions Used for Purification

Column: Chiralpak IC 250×20 mm, 5 um (LOT # IC00CJ-RC003; Part #83345). Mobile phase; n-Hexane:Ethanol:DEA (95:5:0.1% v/v/v).

Compound 8 Enantiomer 1:

MS (MM) m/z: 391.1[M+H]⁺.

Chiral HPLC: 99.1%,

¹H NMR (300 MHz, DMSO-d₆): δ 11.70 (s, 1H), 9.21 (s, 1H), 8.34 (s, 1H), 7.80 (d, J=7.8 Hz, 2H), 7.69 (s, 1H), 7.67 (d, J=1.5 Hz, 1H), 7.49-7.40 (m, 3H), 7.27 (t, J=7.5 Hz, 1H), 7.16 (dd, J=9.0, 2.1 Hz, 2H), 7.12 (s, 1H), 1.46-1.37 (m 1H), 1.27-1.22 (m, 1H), 1.09 (t, J=6.0 Hz, 1H), 0.97 (d, J=6.0 Hz, 3H).

Compound 8 Enantiomer 2:

MS (MM) m/z: 391.1[M+H]⁺.

Chiral HPLC: 97.9%,

¹H NMR (300 MHz, DMSO-d₆): δ 11.69 (s, 1H), 9.20 (s, 1H), 8.34 (s, 1H), 7.80 (d, J=7.8 Hz, 2H), 7.69 (s, 2H), 7.67 (d, J=1.2 Hz, 1H), 7.49-7.40 (m, 3H), 7.27 (t, J=7.2 Hz, 1H), 7.16 (dd, J=9.0, 2.1 Hz, 2H), 7.12 (s, 1H), 1.46-1.37 (m, 1H), 1.27-1.22 (m, 1H), 1.09 (t, J=6.0 Hz, 1H), 0.97 (d, J=6.0 Hz, 3H).

Example 9: Preparations of Compounds 9-11

Using the general methodology disclosed for preparing Compound 8 and general knowledge in organic synthesis, compounds 9-11 in the following table were prepared.

| Compound # | Structure |
|---|---|
| 9 | 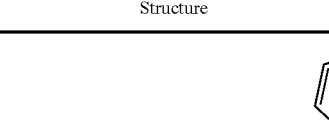<br>enantiomer 1 & enantiomer 2 |

| Compound # | Structure |
|---|---|
| 10 | 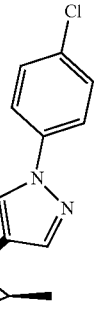<br>enantiomer 1 & enantiomer 2 |
| 11 | 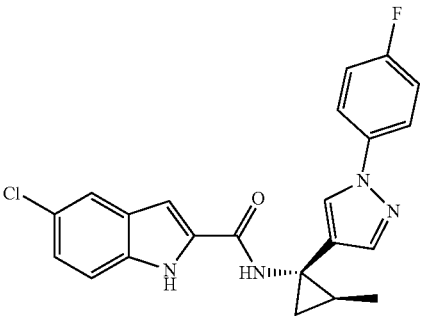<br>enantiomer 1 & enantiomer 2 |

Example 10: Synthesis of Compound 12

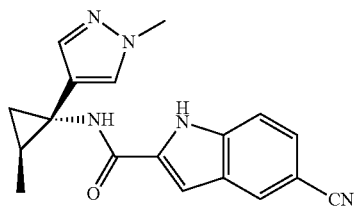 [SMILES: C[C@H]1C[C@@]1(NC(=O)c1cc2cc(C#N)ccc2[nH]1)c1cnn(C)c1]

To a 20 mL vial containing 5-cyano-1H-indole-2-carboxylic acid (250 mg, 1.34 mmol) and HATU (664 mg, 1.75 mmol) was added DMF (5040 µl). The reaction was stirred at room temperature for 5 minutes. Then (1R,2R)-2-methyl-1-(1-methyl-1H-pyrazol-4-yl)cyclopropanamine (229 mg, 1.52 mmol) dissolved in DMF (1680 µl) was added to the activated acid reaction mixture followed by diisopropylethylamine (DIPEA) (1060 µl, 6.04 mmol). The reaction mixture was stirred at room temperature for 30 minutes, then diluted with ethyl acetate, and washed with saturated NaHCO₃. The combined organics were dried over anhydrous magnesium sulfate, filtered, and concentrated in vacuo to give an oil.

The crude product was purified by column chromatography, eluting with a gradient of 100% Hexanes to 100% Ethyl Acetate. The oil obtained was further purified by achiral SFC (column: Chiralcel OJ-H, 21×250 (mm); Modifier: Methanol +0.25% Dimethyl Ethyl Amine; % modifier in CO2:20) to afford 5-cyano-N-((1R,2R)-2-methyl-1-(1-methyl-1H-pyrazol-4-yl)cyclopropyl)-1H-indole-2-carboxamide as a solid to afford Compound 12.

MS ESI calcd. for $C_{18}H_{17}N_5O$ $[M+H]^+$ 320, found 320.
$^1$H NMR (600 MHz, DMSO-$d_6$) δ 12.06 (s, 1H), 9.25 (s, 1H), 8.21 (s, 1H), 7.57-7.49 (m, 3H), 7.33 (s, 1H), 7.24 (s, 1H), 3.77 (s, 3H), 1.35-1.30 (m, 1H) 0.92-0.88 (m, 5H).

Biological Assays

For REF1-REF3 and Compounds 1-11, two different types of assay were employed: 1. An IDO biochemical coupled assay which utilised recombinantly produced and purified IDO enzyme in combination with the enzyme formamidase. This coupled enzyme system allowed conversion of N-formylkynurenine produced by IDO activity to kynurenine which was then quantified by fluorescence following addition of Erhlich's Reagent. 2. A cell-based assay for detecting the effect of test compounds on kynurenine production in cancer cells. This assay utilised cancer cells which expressed IDO and as such was used as a means of testing compound activity at the enzyme in a cell-based context. The protocols for these are set out below.

IDO Biochemical Assays 0.17 µM of human IDO protein was pre-incubated for 120 min at RT with test compounds in the presence of 50 mM KPO₄, pH 7.0, 0.5 mM EDTA, 0.5 mM EGTA, 0.05% Triton X-100, 20 mM ascorbate, 500 U/ml catalase, 10 µM methylene blue at RT in a 384 well plate. 0.05 µg/µl kynurenine formamidase and 45 µM L-tryptophan (L-Trp) were added and the assays were incubated at RT for 40 min. Assays were stopped and the level of kynurenine was determined by incubation with Ehrlich's reagent to a final concentration of 1.33% at RT for 5 min. Fluorescence intensity was read at 475 nm/530 nm.

IDO Cell-Based Assay

SKOV-3 ovary adenocarcinoma (ATCC) cells were grown in McCoys 5A+L-glutamax medium supplemented with 15% foetal bovine serum. On the day of assay, cells were detached using trypsin-EDTA (0.25% v/v), re-suspended in assay media (RPMI 1640 phenol red free+L-glutamine supplemented with 10% dialysed foetal bovine serum). SKOV-3 cells were seeded at 40K cells per well into 96-well plates containing test samples/vehicle control together with 500 µM L-Trp. Cells were then incubated for 48 h at 37° C. 5% CO₂. IFNγ was also added at 500 ng/ml for the 48 h incubation in order to induce expression of IDO. Plates were centrifuged and the supernatant was removed and incubated for 5 min in the presence of 1% Erhlich's reagent. Kynurenine levels were then quantified by measuring absorbance at 490 nm.

The pIC50 values for REF1-REF3 and Compounds 1-11 are shown in Table 1.

TABLE 1 pIC50 values for the inhibition of IDO (SKOV-3 cells)

| Compound | pIC$_{50}$, IDO cellular assay (SKOV3) |
|---|---|
| REF 1 | 6.90 |
| REF 2 | 6.73 |
| REF 3 | 6.74 |
| Compound 1, (+) 1 | 7.38 |
| Compound 1, (−) 1 | 6.44 |
| Compound 1, racemic | 7.10 |
| Compound 2, (−) 2 | 6.55 |
| Compound 2, (+) 2 | 7.67 |
| Compound 2, racemic | 7.50 |
| Compound 3 | 7.05 |
| Compound 4 | 7.06 |
| Compound 5 | 7.04 |
| Compound 6 | 7.08 |
| Compound 7, racemic | 7.06 |
| Compound 8, enantiomer 1 | 7.73 |

TABLE 1-continued pIC50 values for the inhibition of IDO (SKOV-3 cells)

| Compound | pIC$_{50}$, IDO cellular assay (SKOV3) |
| --- | --- |
| Compound 8, enantiomer 2 | 7.83 |
| Compound 9, enantiomer 1 | 7.11 |
| Compound 9, enantiomer 2 | 7.36 |
| Compound 10, enantiomer 1 | 7.46 |
| Compound 10, enantiomer 2 | 7.93 |
| Compound 11, enantiomer 1 | 7.55 |
| Compound 11, enantiomer 2 | 8.00 |

The Table shows that the tested compounds show strong IDO inhibitory function in cell-based assays. This compares with the REF compounds, which scored less well on each of the tests.

Biochemical enzyme assays were conducted according to the protocols described above, and the results confirmed the bona fide activity of the compounds as enzyme inhibitors. The results are shown in Table 2.

TABLE 2 pIC50 values for IDO inhibition for REF1-REF3 and Compounds 1-7

| Compound | hIDO biochemical assay pIC50 |
| --- | --- |
| REF 1 | 5.42 |
| REF 2 | 5.17 |
| REF 3 | 5.84 |
| Compound 1, (+) 1 | 6.40 |
| Compound 1, (−) 1 | 5.77 |
| Compound 1, racemic | 5.90 |
| Compound 2, (−) 2 | 5.54 |
| Compound 2, (+) 2 | 6.42 |
| Compound 2, racemic | 6.40 |
| Compound 3 | 6.36 |
| Compound 4 | 6.35 |
| Compound 5 | 4.84 |
| Compound 6 | 5.96 |
| Compound 7, racemic | 5.87 |

IDO1 Cellular Assay for Compound 12

Compounds to be tested were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 550 acoustic liquid handler (Labcyte).

HEK293 cell pellets were resuspended to 5×10$^5$ cells/mL in complete HEK293 culture media (89% DMEM, 10% FBS, 1% penicillin/streptomycin). Suspended cells (2 mL) were dispensed into each well of a 6-well Corning plate (Catalog#3516). Cells were allowed to attach and were incubated for 20 hours at 37 degrees Celcius in a 5% CO$_2$ incubator. Flag-IDO1 vector (Genscript True ORF Gold, 2 ug) in 150 uL of Opti-MEM medium was added to to each well of a Corning 24 well plate (Cat#3527) and incubated for 5 minutes at room temperature. To each well of the 24-well plate was added 150 μL Lipofectamine 2000 (Gibco) and the plate incubated at room temperature for 20-30 minutes. To each well of attached cells in the 6-well plate, 250 μL of the transfection mix from the 24-well plate was gently added to each well and IDO1 protein was allowed to express for 24-30 hours at 37 degrees Celcius in a 5% CO$_2$ incubator.

Media was removed from the cells which were then washed with 2 mL Dulbecco's phosphate-buffered saline (DPBS). After removal of DPBS, 0.5 mL of TrypLE (Gibco) was added and incubated at 5 minutes until cells lift from the surface of the wells. Complete HEK293 culture media (4 mL) was added to each well and cells were collected and pooled into a conical tube. Cells were pelleted at 200×g for 5 minutes and resuspended in an equal volume of complete DMEM medium. Cells were diluted to 4×10$^5$ cells per mL in complete HEK293 media. L-Tryptophan was added to give a final concentration of 200 μM. The diluted transfected cells (50 μL) or nontransfected cells (50 μL) were dispensed into wells of Greiner black 384-well assay plates (catalog #781086) containing previously diluted compounds. The plate is briefly mixed and centrifuged at 200×g for 10 seconds to collect cells at the bottom of the plate. Plates were covered and incubated for 20-24 hours at 37 degrees C. in a 5% CO$_2$ incubator. Afterwards 10 μL of 0.5 M methyl isonipecotate in dimethyl sulfoxide was added to each well, mixed, sealed, and centrifuged at 500 rpm for 10 seconds. Plates were incubated at 37 degrees in a 5% CO$_2$ incubator overnight to develop fluorescence. The plates are allowed to cool and then centrifuged for 1 minute at 1000×g. The resulting fluorescence was measured in an Envision plate reader (Perkin Elmer) with a 400/25 nm excitation filter and an 510/20 nm emission filter.

The fluorescence intensity of each well was corrected for the background observed in wells with untransfected cells and was expressed as a fraction of the intensity observed in wells of IDO1 transfected cells and DMSO only. Potencies were calculated by linear least squares fit to the four parameter logistic IC$_{50}$ equation.

Using the above assay, Compound 12 has an IC50 of 202 nM (n=1) in the HEK293 cell line transiently expressing hIDO1.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

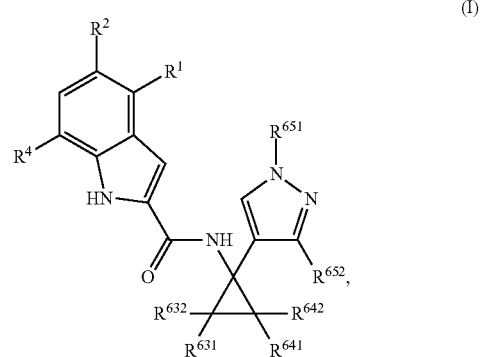

(I)

wherein R$^2$ is selected from Cl, —Br and —CN;
R$^1$ and R$^4$ are independently selected from —H and —F;
R$^{631}$, R$^{632}$, R$^{641}$ and R$^{642}$ are independently selected from —H, —F and C$_1$-C$_3$ alkyl;
R$^{651}$ and R$^{652}$ are independently selected from —H, and C$_1$-C$_3$ alkyl; and
wherein at least one of R$^{631}$, R$^{632}$, R$^{641}$, and R$^{642}$ is not —H.

2. The compound according to claim 1, or a pharmaceutically acceptable salt thereof, which compound is a compound of the following formula:

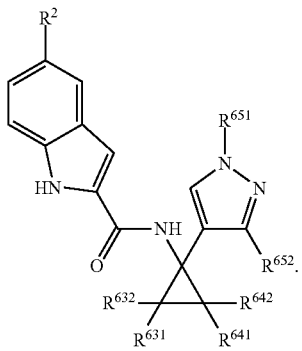

3. The compound according to claim 1, or a pharmaceutically acceptable salt thereof, which compound is a compound of the following formula:

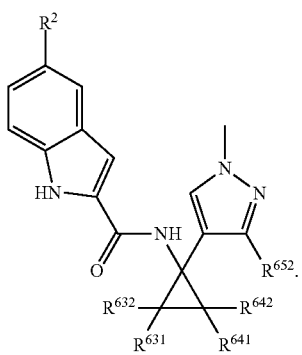

4. The compound according to claim 1, or a pharmaceutically acceptable salt thereof, which compound is a compound of the following formula:

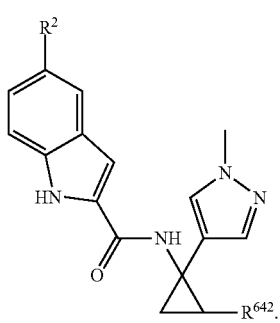

wherein $R^{642}$ is methyl or ethyl.

5. The compound according to claim 1, or a pharmaceutically acceptable salt thereof, which compound is a compound of one of the following formulae:

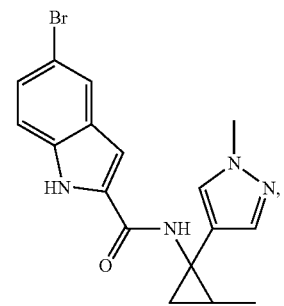

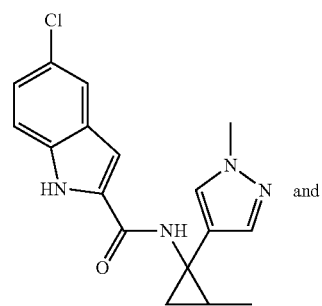

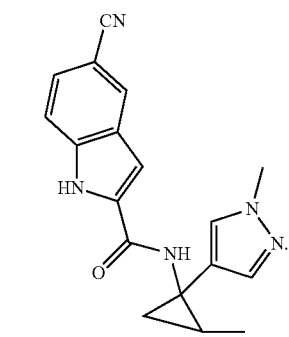

6. The compound according to claim 1, or a pharmaceutically acceptable salt thereof, which compound is an isolated enantiomer or a racemic mixture of one or both of the following formula:

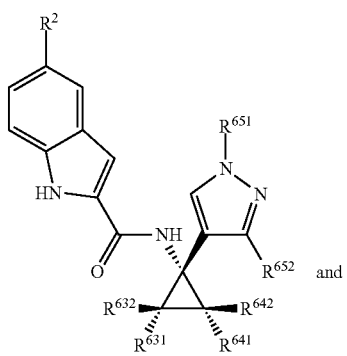

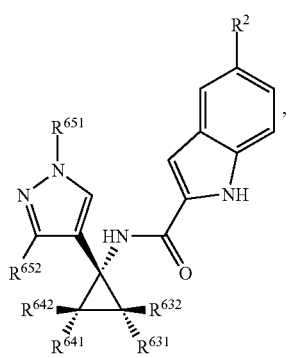

wherein R⁶⁴² is a sterically larger group than any of R⁶³¹, R⁶³² and R⁶⁴¹.

7. The compound according to claim 1, which compound is an isolated enantiomer or a racemic mixture of one or both of the following formulae:

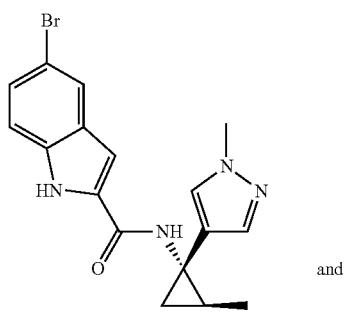

and

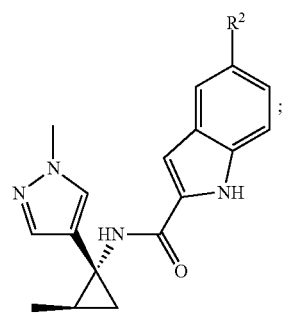

;

or one or both of one of the following formulae:

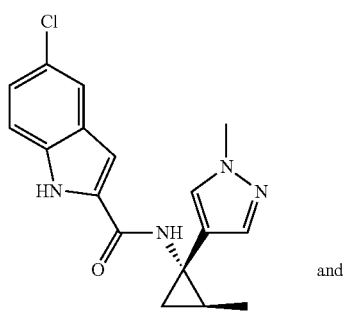

and

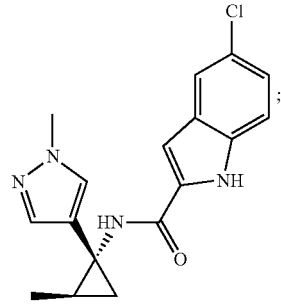

;

or one or both of one of the following formulae:

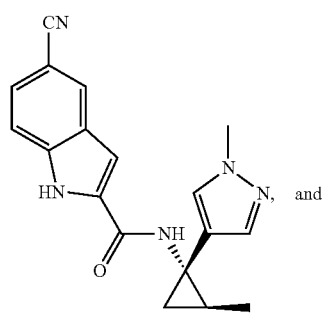

, and

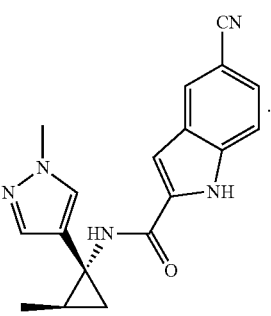

.

8. The compound according to claim 1, which is an isolated enantiomer, a racemic mixture or an achiral compound of any of the following formulae:

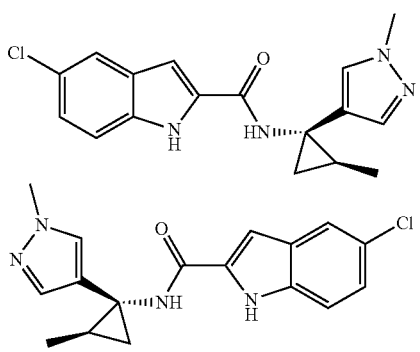

isolated (+) and (−) enantiomers and racemic mixture 1: [(+) 1, (−) 1 and rac 1],

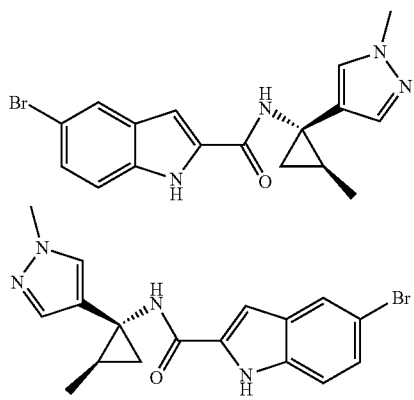

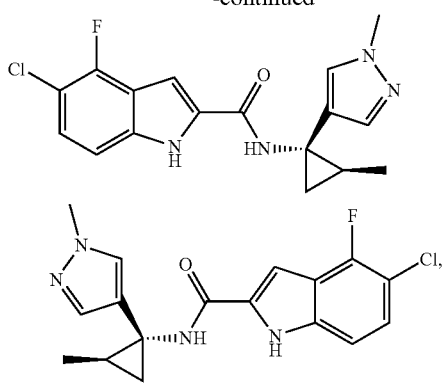

isolated (+) and (−) enantiomers and racemic mixture 2: [(+) 2, (−) 2 and rac 2], isolated (+) and (−) enantiomers and racemic mixture 7: [(+) 7, (−) 7 and rac 7],

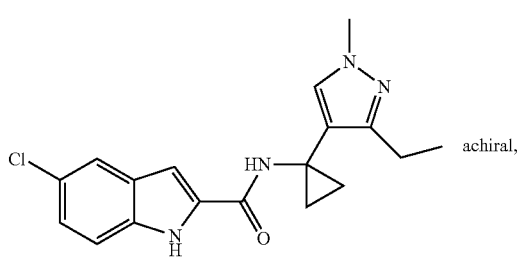 achiral,

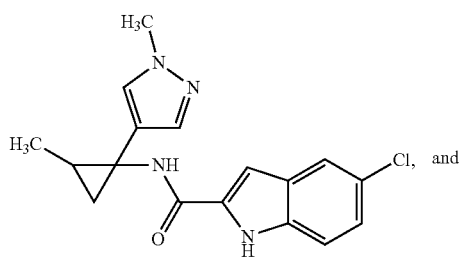 and

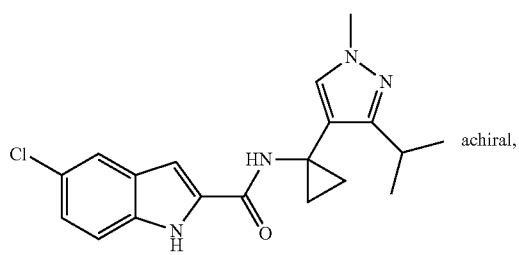 achiral,

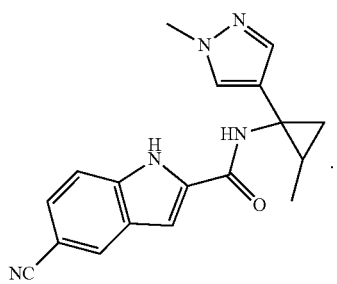

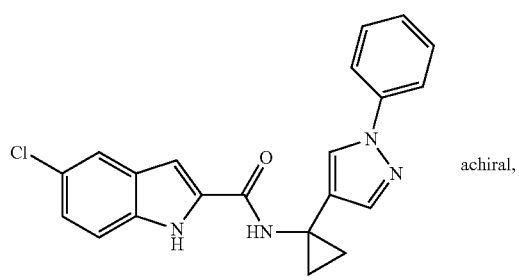 achiral,

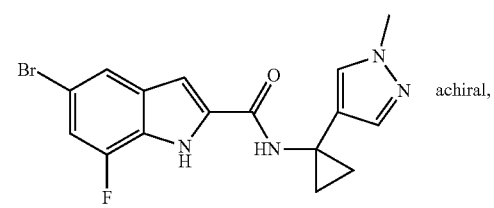 achiral,

9. A pharmaceutical composition comprising a compound of claim 1, or a pharmaceutically acceptable salt thereof, and a pharmaceutical excipient.

10. The pharmaceutical composition according to claim 9, further comprising a pharmaceutically acceptable additive.

11. The pharmaceutical composition according to claim 10, further comprising an agent selected from: an anti-tumour vaccine; a cancer immunotherapy treatment; an immunomodulator; an immunosuppressant; a cytokine therapy; a tyrosine kinase inhibitor; and a chimeric antigen receptor T cell therapy (CAR-T).

* * * * *